US011543400B2

(12) United States Patent
Burgess

(10) Patent No.: US 11,543,400 B2
(45) Date of Patent: Jan. 3, 2023

(54) LIQUID TESTING SYSTEM AND METHOD

(71) Applicant: Validere Technologies Inc., Toronto (CA)

(72) Inventor: Ian Bruce Burgess, Toronto (CA)

(73) Assignee: Validere Technologies Inc., Toronto (CA)

( * ) Notice: Subject to any disclaimer, the term of this patent is extended or adjusted under 35 U.S.C. 154(b) by 391 days.

(21) Appl. No.: 16/485,904

(22) PCT Filed: Feb. 14, 2018

(86) PCT No.: PCT/CA2018/050167
§ 371 (c)(1),
(2) Date: Aug. 14, 2019

(87) PCT Pub. No.: WO2018/148829
PCT Pub. Date: Aug. 23, 2018

(65) Prior Publication Data
US 2020/0041481 A1 Feb. 6, 2020

Related U.S. Application Data

(60) Provisional application No. 62/588,842, filed on Nov. 20, 2017, provisional application No. 62/458,728, filed on Feb. 14, 2017.

(51) Int. Cl.
*G01N 33/28* (2006.01)
*G01N 7/06* (2006.01)
*G01N 9/04* (2006.01)

(52) U.S. Cl.
CPC ............... *G01N 33/28* (2013.01); *G01N 7/06* (2013.01); *G01N 9/04* (2013.01)

(58) Field of Classification Search
CPC .................................. G01N 7/06; G01N 9/04
See application file for complete search history.

(56) References Cited

U.S. PATENT DOCUMENTS

| | | | | |
|---|---|---|---|---|
| 2012/0011919 A1* | 1/2012 | Kriel | ...................... | G01N 30/88 73/23.35 |
| 2012/0127466 A1* | 5/2012 | Karnes | ............... | G01N 33/2811 356/319 |
| 2013/0199286 A1* | 8/2013 | Gao | ........................ | E21B 49/08 73/152.27 |
| 2014/0175083 A1* | 6/2014 | Bhaidasna | ........... | H05B 1/0269 219/386 |

OTHER PUBLICATIONS

International Search Report and Written Opinion of the International Searching Authority dated May 3, 2018 in corresponding International application No. PCT/CA2018/050167; 10 pages.

(Continued)

*Primary Examiner* — Daniel S Larkin
(74) *Attorney, Agent, or Firm* — Maier & Maier, PLLC

(57) ABSTRACT

The present application provides a method and system for the characterization of properties of liquids, particularly petroleum and petroleum liquids. The method and system can be used to take measurements of the liquid directly in a storage container, without exposing the contents of the container to the external environment.

24 Claims, 33 Drawing Sheets

Schematic of the overall device concept. A sample container collects the sample and then is connected to a reader. The reader performs a measurement on the sample without requiring the transfer of any liquid from the sample container

(56) References Cited

OTHER PUBLICATIONS

Lineironic Technologies, "Gage Vapour Pressure of LPG", Apr. 4, 2016; retrieved online on Apr. 13, 2018 from: https://web.archive.org/web/20160404154517/http://www.lin-tech.ch/english/vp174000eng.html; 3 pages.

WIKA Corporate, Press Release "Configure and read instruments via app and smartphone", Oct. 2016; retrieved online on Apr. 13, 2018 from: http://en.wika.com/upload/PR_1316_pdf_en_co_76875.pdf; 2 pages.

Zhao et al., "Pressure drop and friction factor of a rectangular channel with staggered mini pin fins of different shapes", Experimental Thermal and Fluid Science, Feb. 2016, vol. 71, p. 57-69; 13 pages.

Littlejohn et al., "Vapor Pressure Measurement System for Heavy Crude Oils", Journal of the Air & Waste Management Association, 49:9, p. 1103-1109; 8 pages.

\* cited by examiner

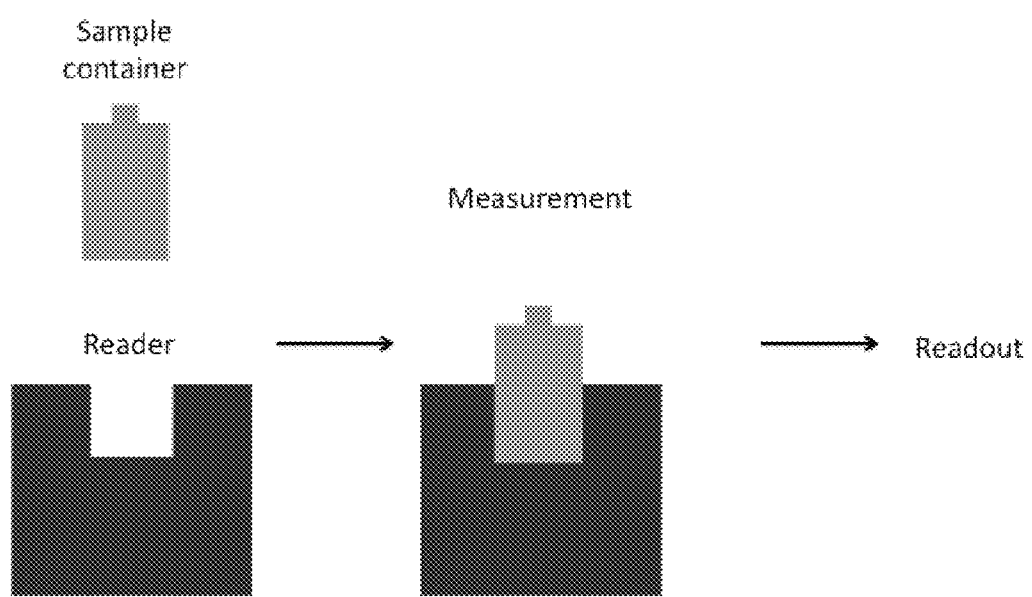
Figure 1 – Schematic of the overall device concept. A sample container collects the sample and then is connected to a reader. The reader performs a measurement on the sample without requiring the transfer of any liquid from the sample container

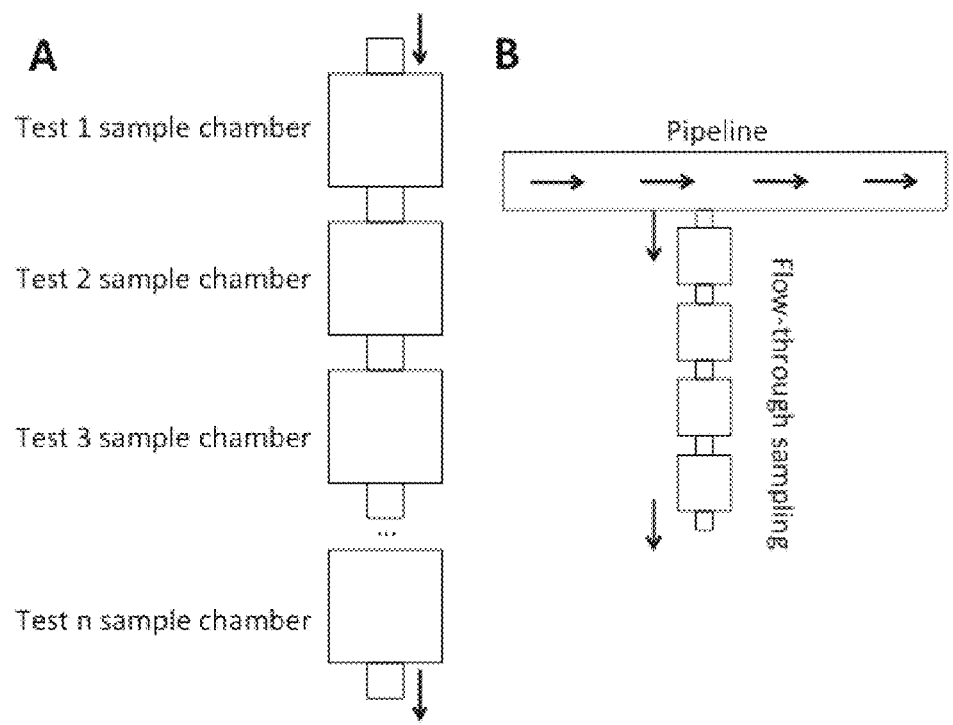
Figure 2 -- Schematic showing a sample container array. (A) Multiple sample containers can be connected in series,. Each can be designed for a different test or series of tests. (B) Sampling can be done in all chambers together using a flow-through method.

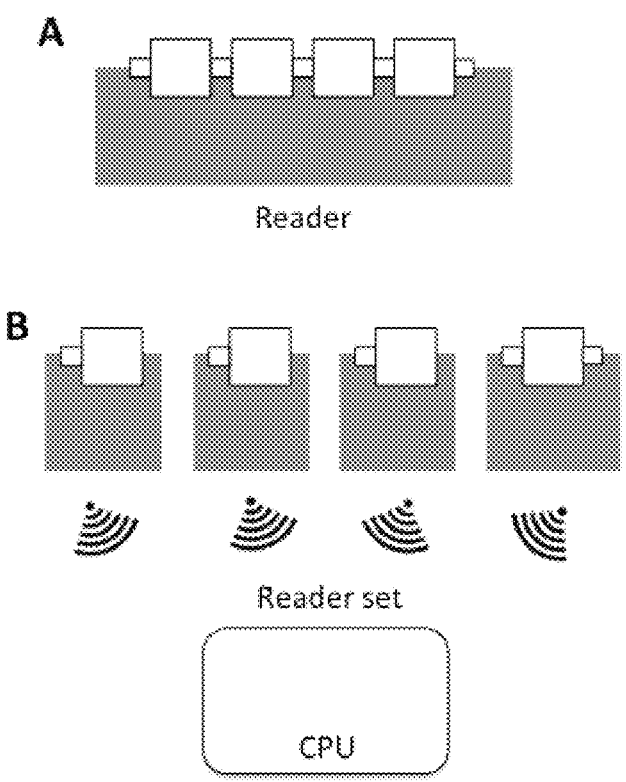

Figure 3 – Schematic of different reader configurations for a sample chamber array. (A) In some embodiments, all chambers may connect to the same reader at different locations. (B) In some embodiments, the chambers may be detached from one another and connected to an array of readers. In some embodiments, each reader communicates with a central processing unit via a physical connection, wireless connection (Bluetooth, wifi, satellite), and/or via the internet.

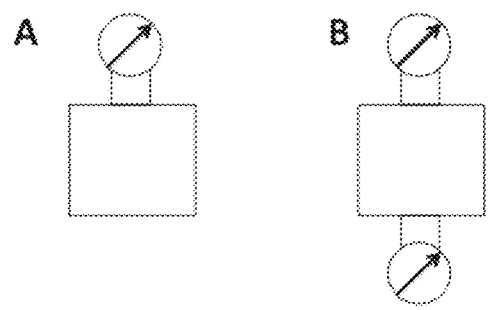
Figure 4 – (A) In some embodiments, the sample container may be capped with a valve or seal at only one end. (B) In some embodiments, the sample container is capped with a valve, cap or seal at two ends to enable flow-through sampling.

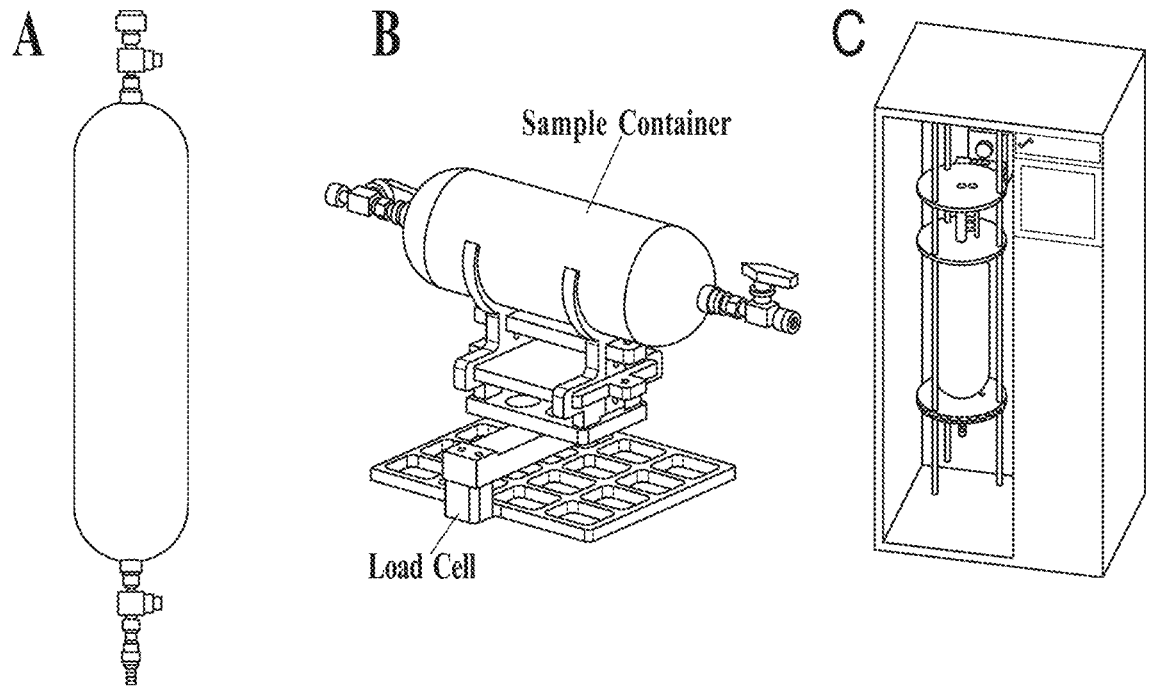

Figure 5 - Schematic of density measurement according to certain embodiments. A sample container completely filled with liquid (A) is placed on an apparatus containing a load cell or strain gauge (B) that measures its mass. The sample container can also be weighed in a hanging configuration (C). Since the sample container is filled at the temperature of the source, measuring the mass of the filled container under any conditions allows the instrument to calculate the density at the temperature of the source. This removes the requirement to control or monitor temperature during measurement.

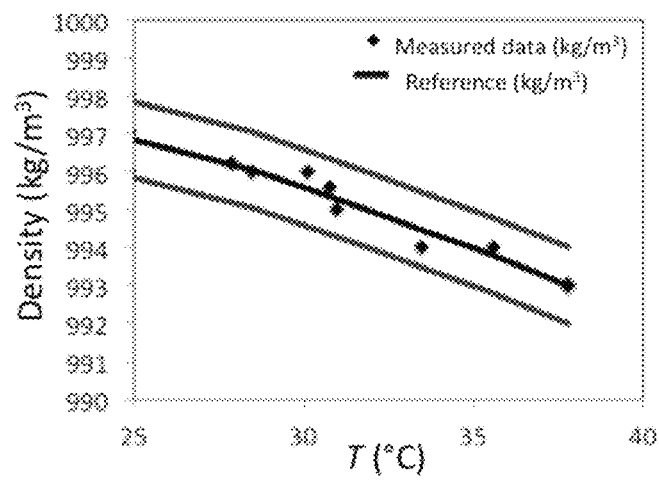
Figure 6 – Density of water measured at different sampling temperatures using the embodiment of Fig. 5. Mass measurements were made at 20C for all samples. Density follows the temperature of sampling, as predicted.

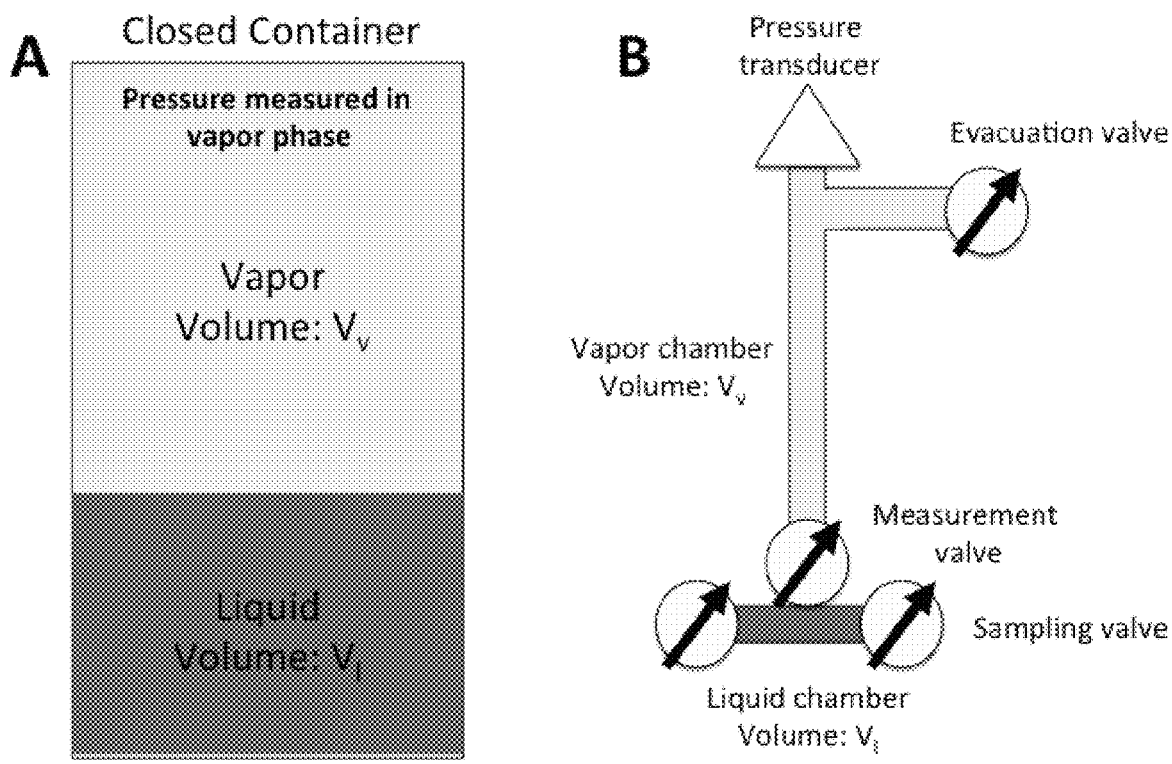

Figure 7 – (A) General schematic of vapour pressure measurement. (B) Schematic of apparatus according to certain embodiments. A liquid chamber with volume (Vl) contains two sampling valves at either end and is connected to a vapor chamber with volume (Vv) by a measurement valve. The vapour chamber contains a pressure transducer. In some embodiments, the vapour chamber also contains an evacuation valve that enables the atmosphere to be preset before a measurement (e.g. as vacuum, air, or another inert gas filled to a given pressure).

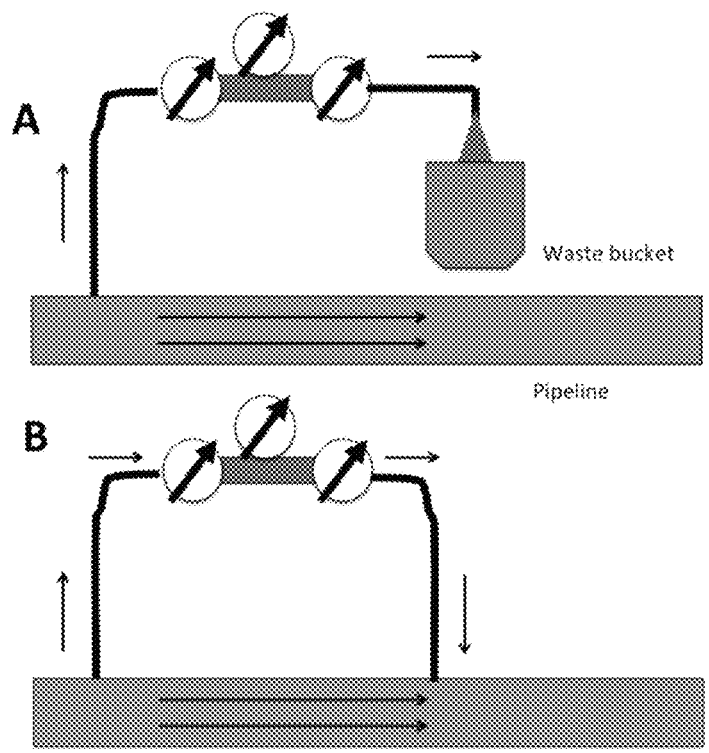

Figure 8 – Schematic of the liquid chamber being filled using a flow-through technique from a pressurized pipeline flow according to certain embodiments. This technique enables the sample to be taken with the pipeline pressure preserved and without being exposed to the outside air. (A) the sample flowing through the container is collected into a waste bucket. (B) The sample flowing through the container is returned to the pipeline.

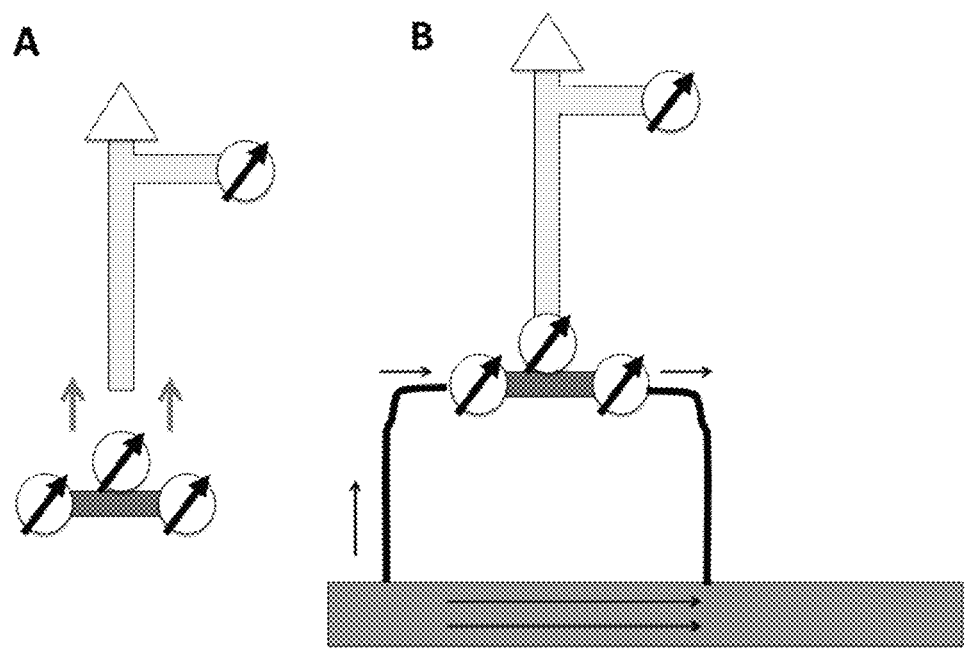
Figure 9 – Configuration of the liquid and vapour chambers according to certain embodiments. (A) In some embodiments, the liquid chamber is detached from the rest of the apparatus during sampling. (B) In some embodiments, the liquid chamber and the vapour chamber remain connected during sampling.

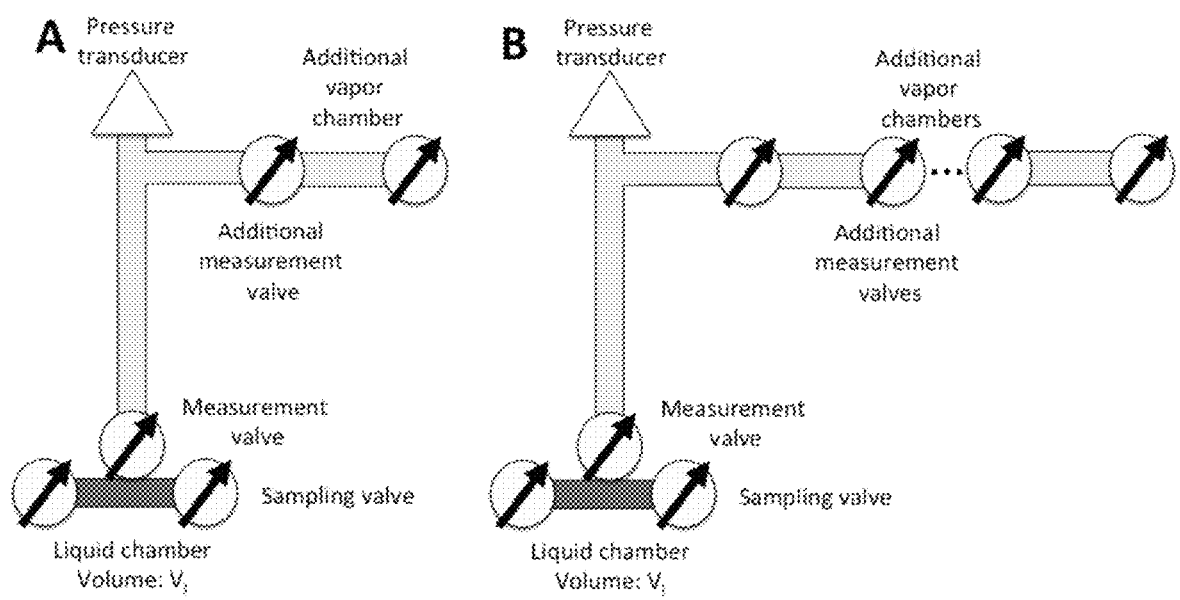
Figure 10 – One (A) or several (B) additional measurement valves enable measurements to be made at multiple V/L ratios.

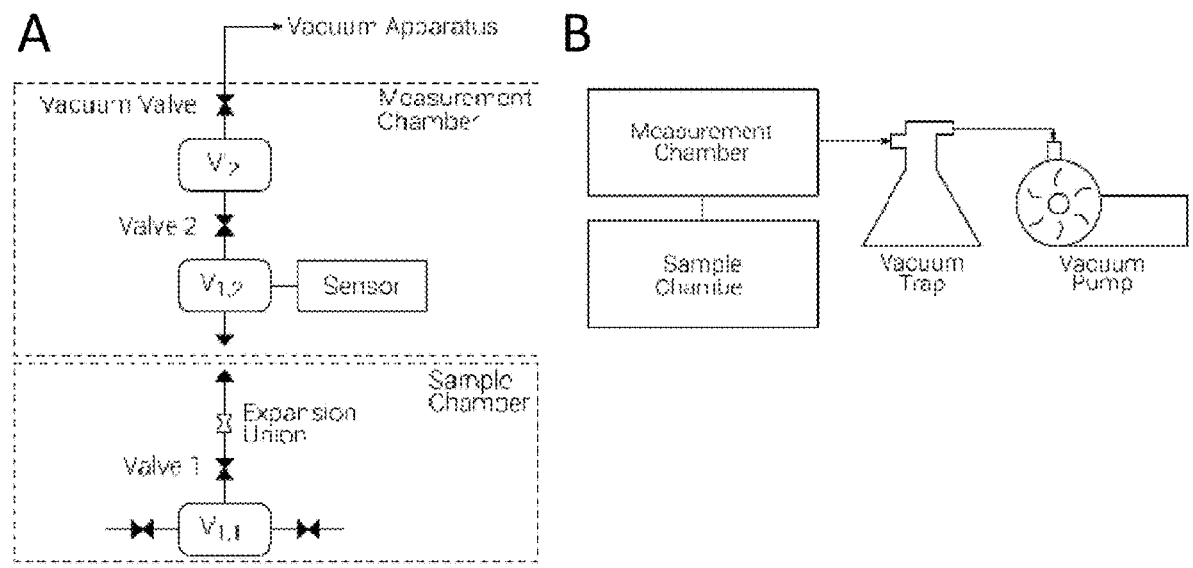

Figure 11 – Configuration of the measurement, sample chambers and connectivity to vacuum apparatus according to certain embodiments. (A) In some embodiments, the sample chamber is detached from the rest of the apparatus during sampling via a quick connecting mechanism. In this embodiment, the measurement chamber is completely evacuated post reattachment of the sample chamber. The sample chamber has an inline feature which eliminates sample splatter upon the instantaneous sample boiling from opening valve 1. Some embodiments feature multiple volumes for multiple expansions: here volume 1 is represented by $V_{1,1} + V_{1,2}$ and volume 2 is be represented by $V_{1,1} + V_{1,2} + V'_2$. (B) In some embodiments, the measurement chamber is evacuated and a complete vacuum is established using a vacuum apparatus prior to vapour expansion. A vacuum trap is used upstream of the vacuum pump to eliminate sample vapour buildup and deterioration of the vacuum pump.

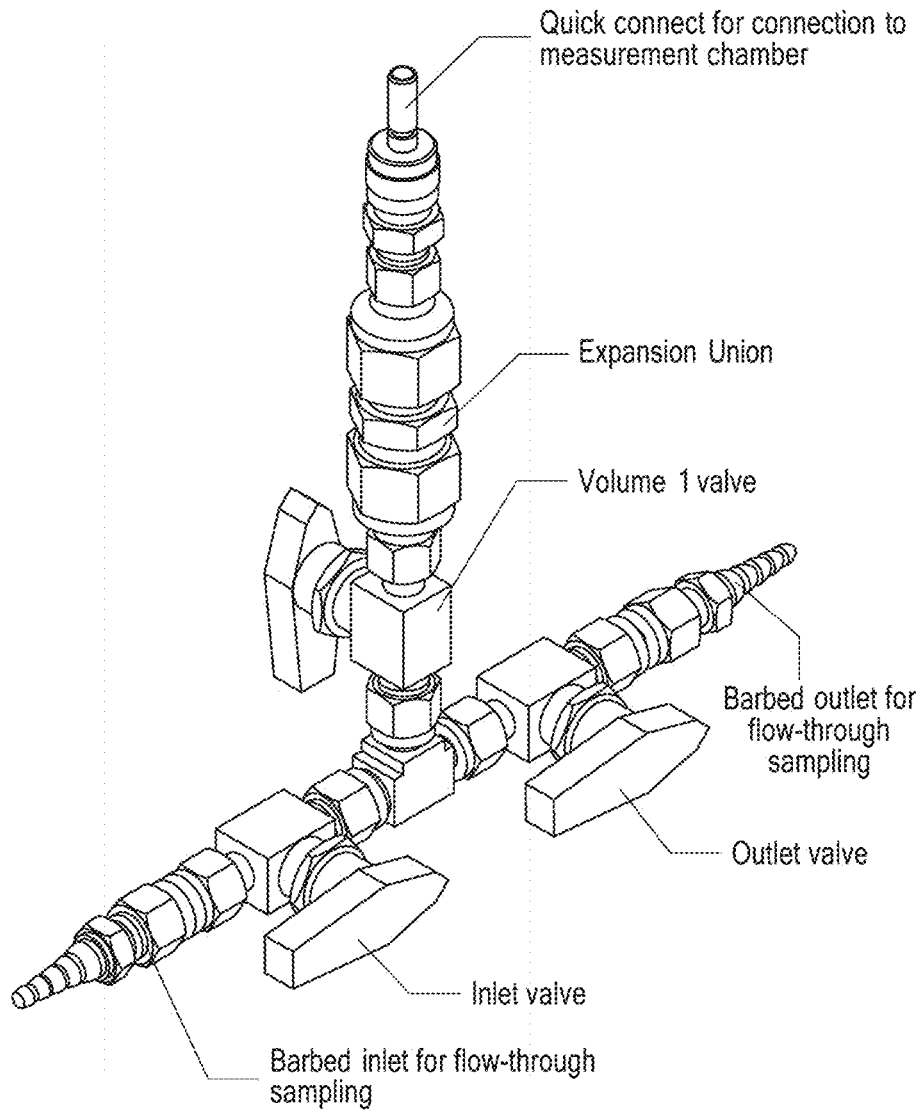

Figure 12B

Model configurations of the measurement chamber 12(A) and the sample chamber 12(B) according to certain embodiments. In some embodiments, the sample chamber features barbed inlets and outlets for flexible tubing connection for flow-through sampling. The inlet and outlet valves are used to control flow into and out of the sample chamber. Volume 1 valve in the sample chamber is used to initiate the vapour expansion and measurement. The inline filter eliminates sample splatter and liquid contamination of downstream components (i.e. the measurement chamber) but permits vapour flow. Quick connection mechanisms on both the sample and measurement chambers allow for ease of repeated use and measurements. Integrated pressure and temperature measurements of the vapour expansion allows for real-time temperature corrections to variable target temperatures. Volume 2 valve is used to increase the volume of the measurement chamber for an additional expansion. Vacuum valve is used to control the venting of the measurement chamber of post measurement.

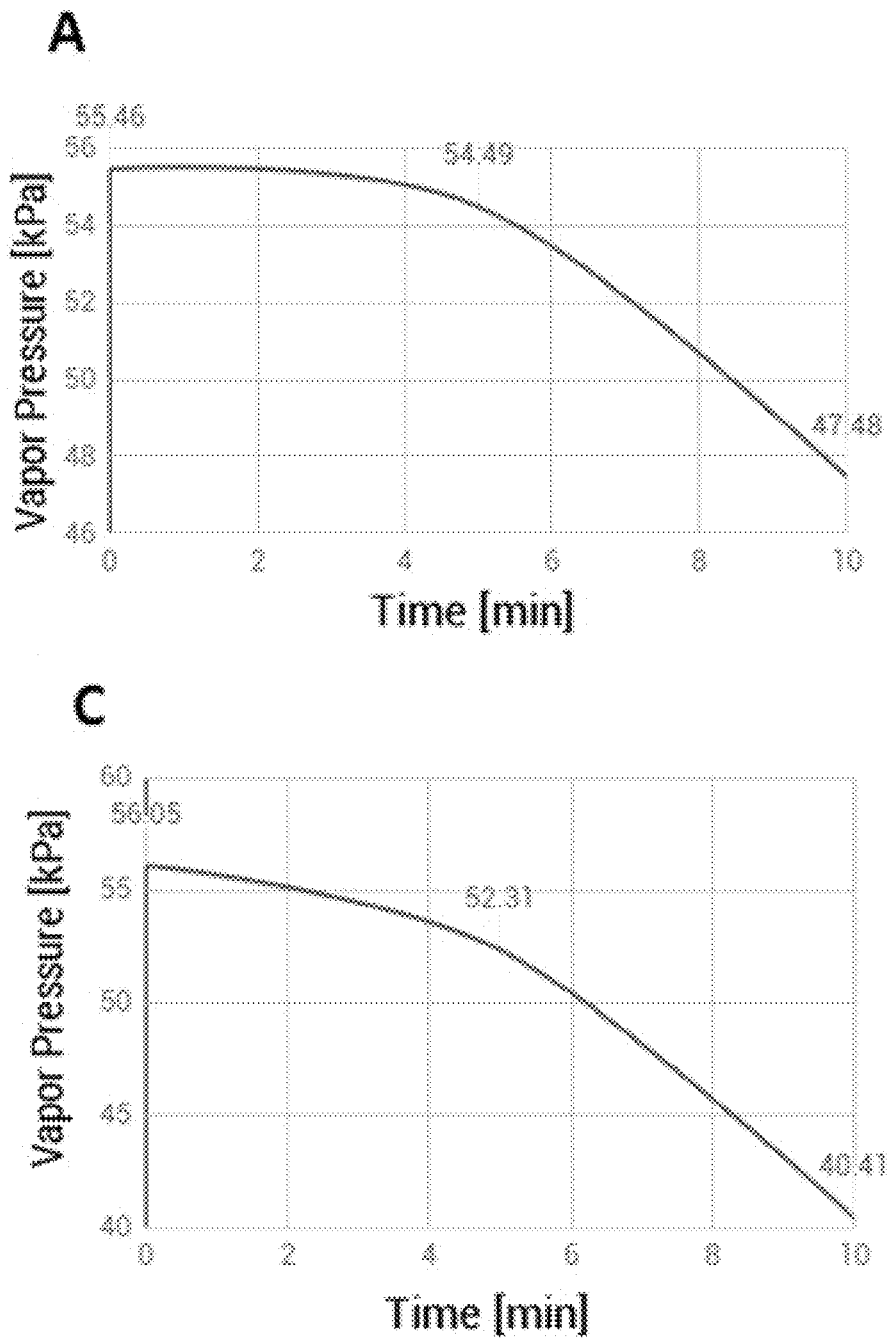
Figure 13 – Measured vapour pressure of various light crude oils (A,C) after being exposed to atmospheric conditions over time. This highlights to minimize sample exposure and to maintain a pressurized environment throughout (i.e. flow-through sampling). This minimizes the loss of light ends and enables more representative vapour pressure measurements.

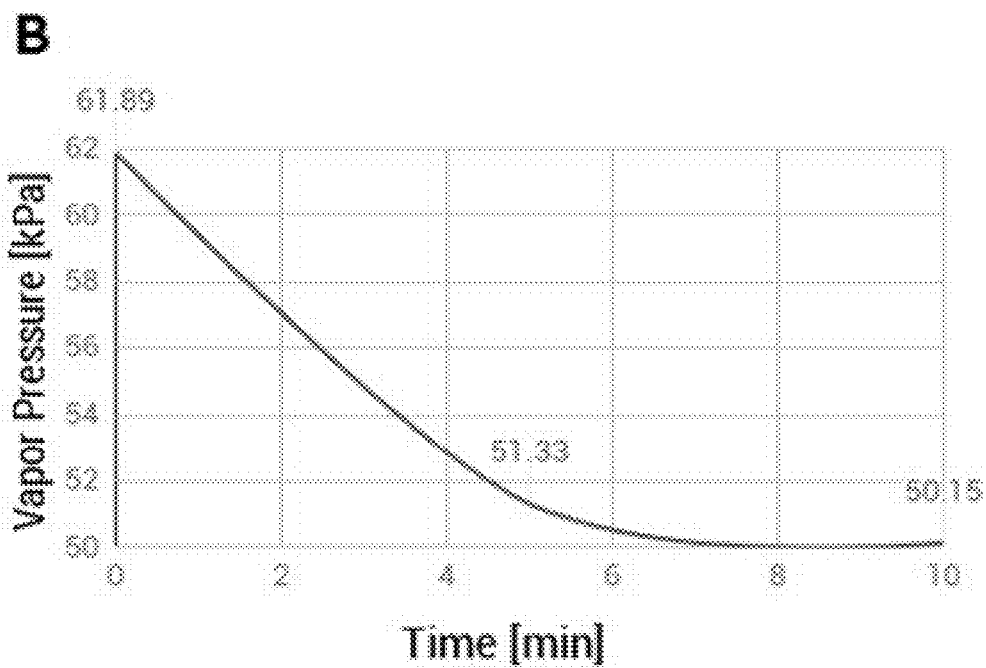
Figure 13 – Measured vapour pressure of condensates (B) after being exposed to atmospheric conditions over time. This highlights to minimize sample exposure and to maintain a pressurized environment throughout (i.e. flow-through sampling). This minimizes the loss of light ends and enables more representative vapour pressure measurements.

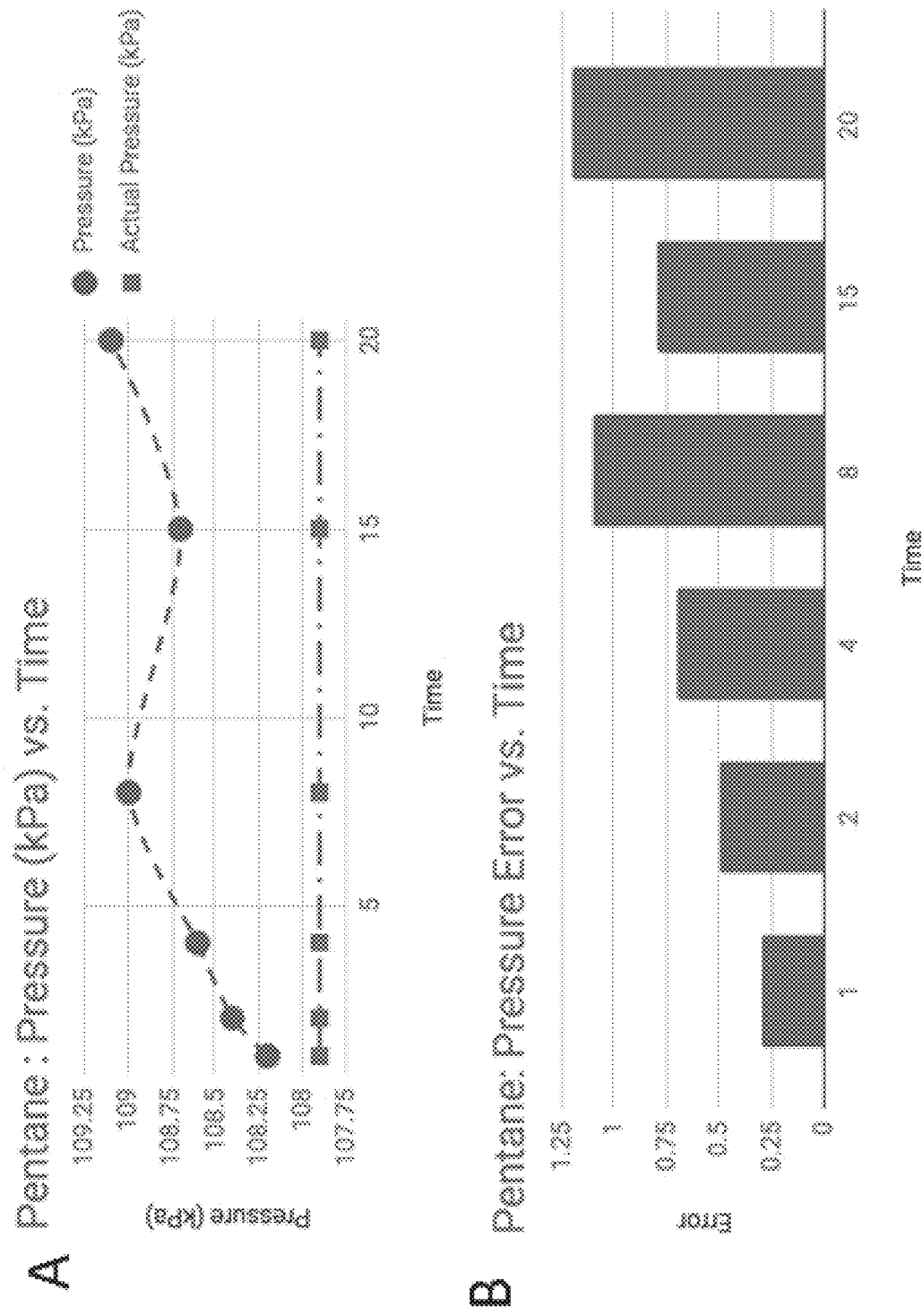
Figure 14 – (A) Measured vapour pressure of pentane over time (circle markers) and comparison to the standard vapour pressure (square markers). (B) Vapour pressure measurement error of pentane relative to standard values over time.

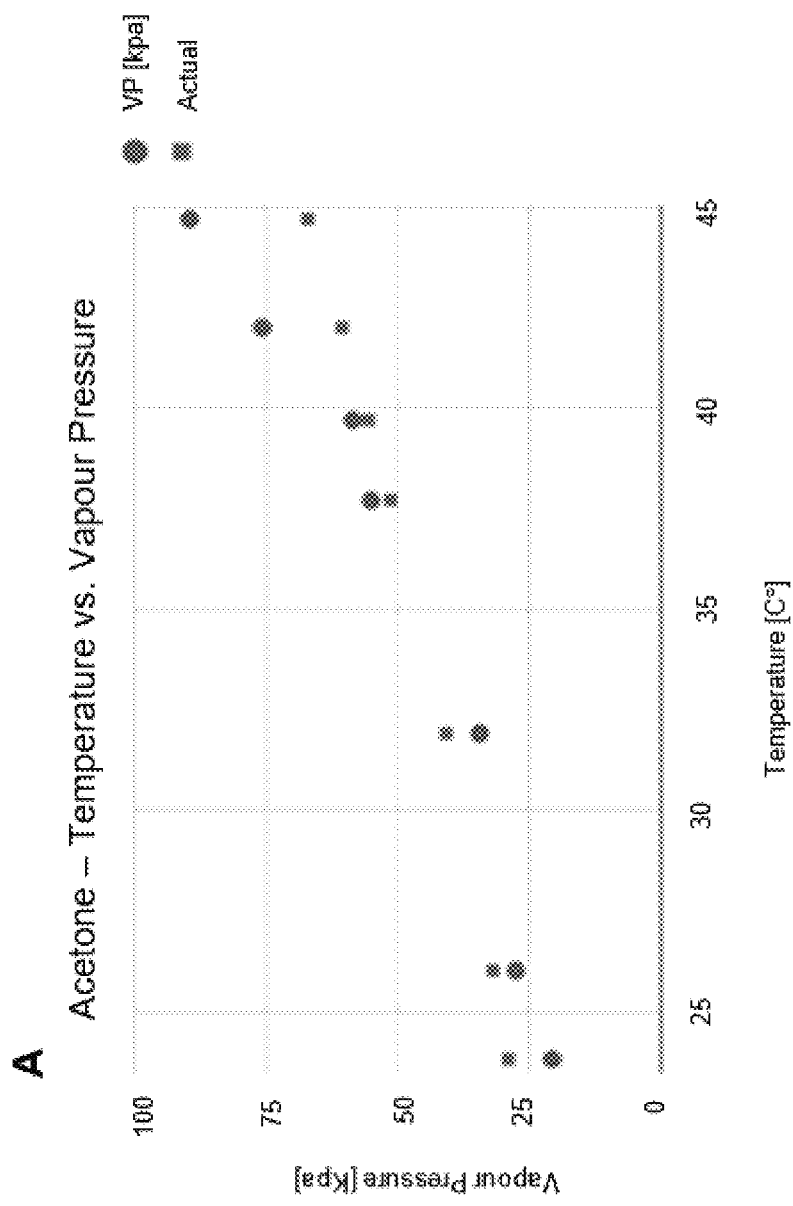
Figure 15 — (A) Measured vapour pressure values for acetone at various controlled temperatures via a water bath and theoretical vapour pressure values.

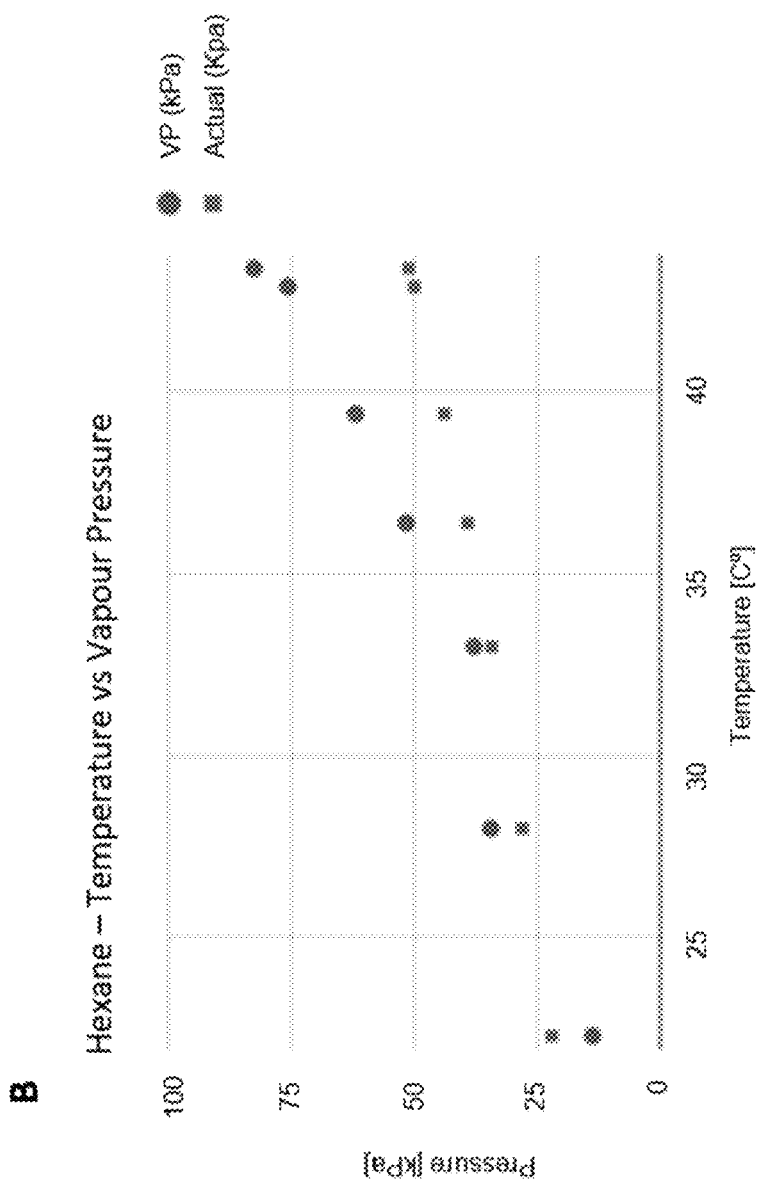
Figure 15 —(B) Similar vapour pressure comparisons at variable temperatures for hexane.

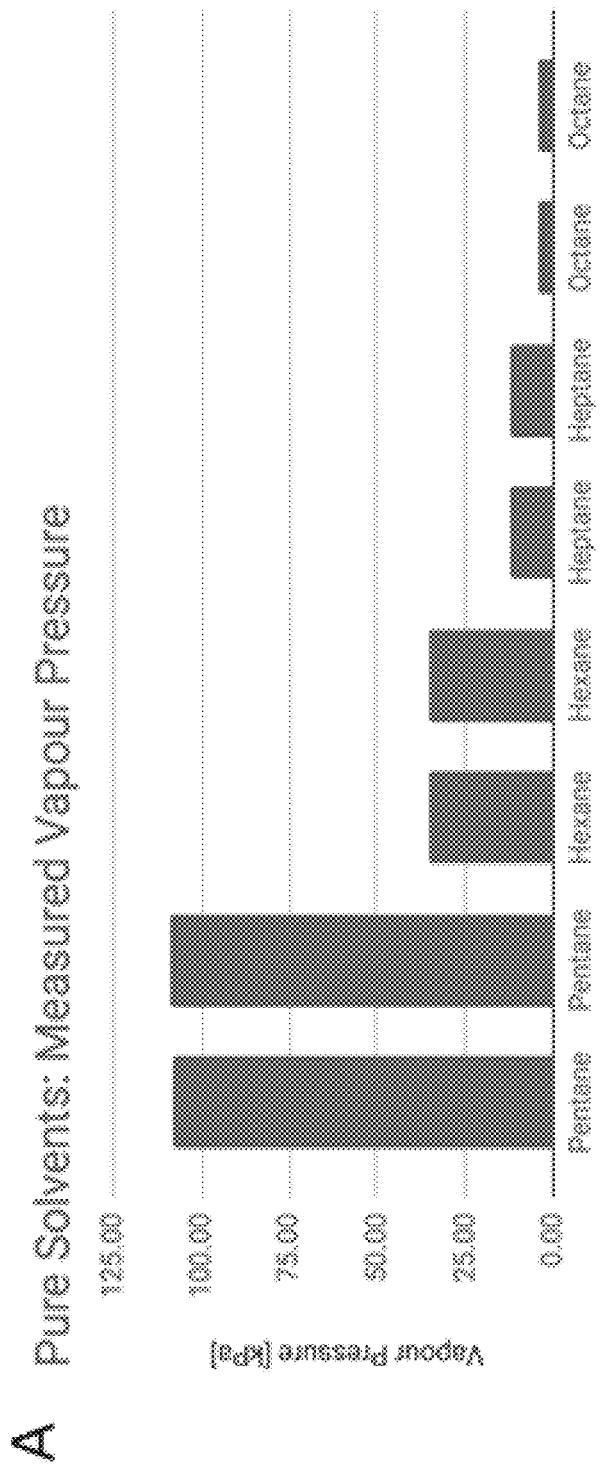
Figure 16 – (A)Vapour pressure measurements for various pure alkanes.

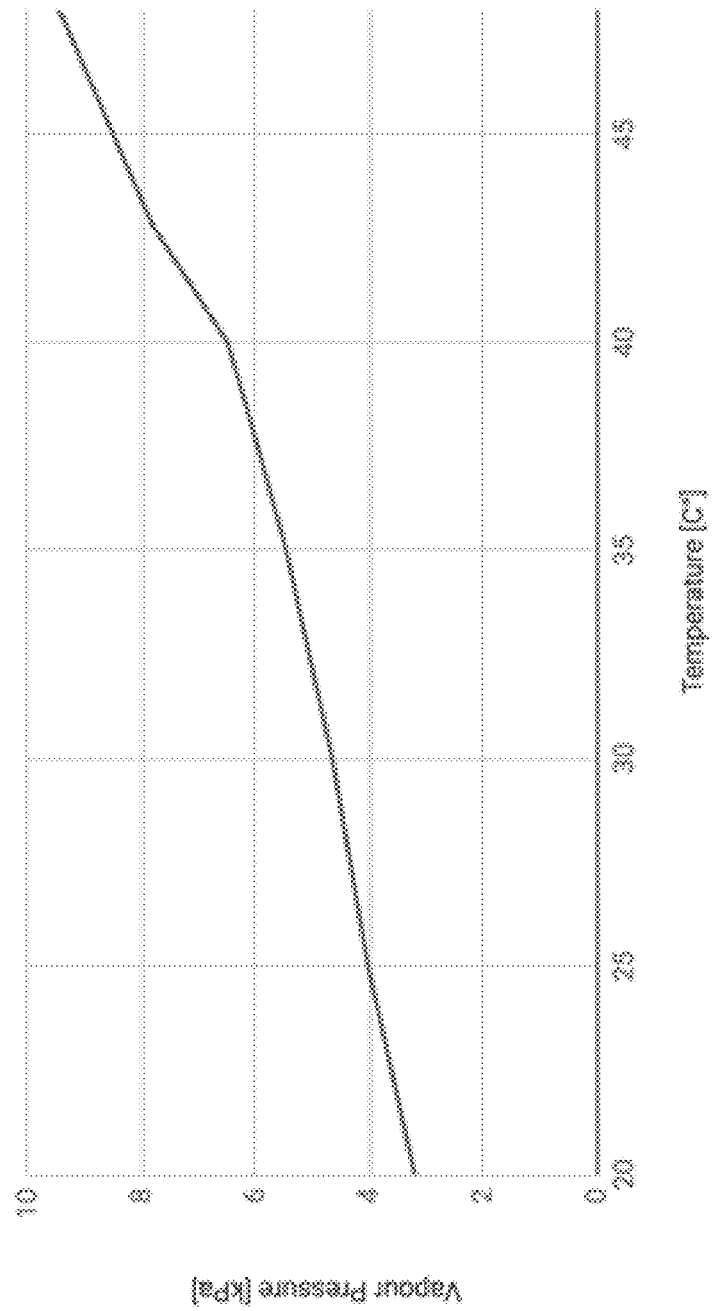
Figure 16 – (B) Temperature-Vapour pressure curve for octane constructed using measured vapour pressure values.

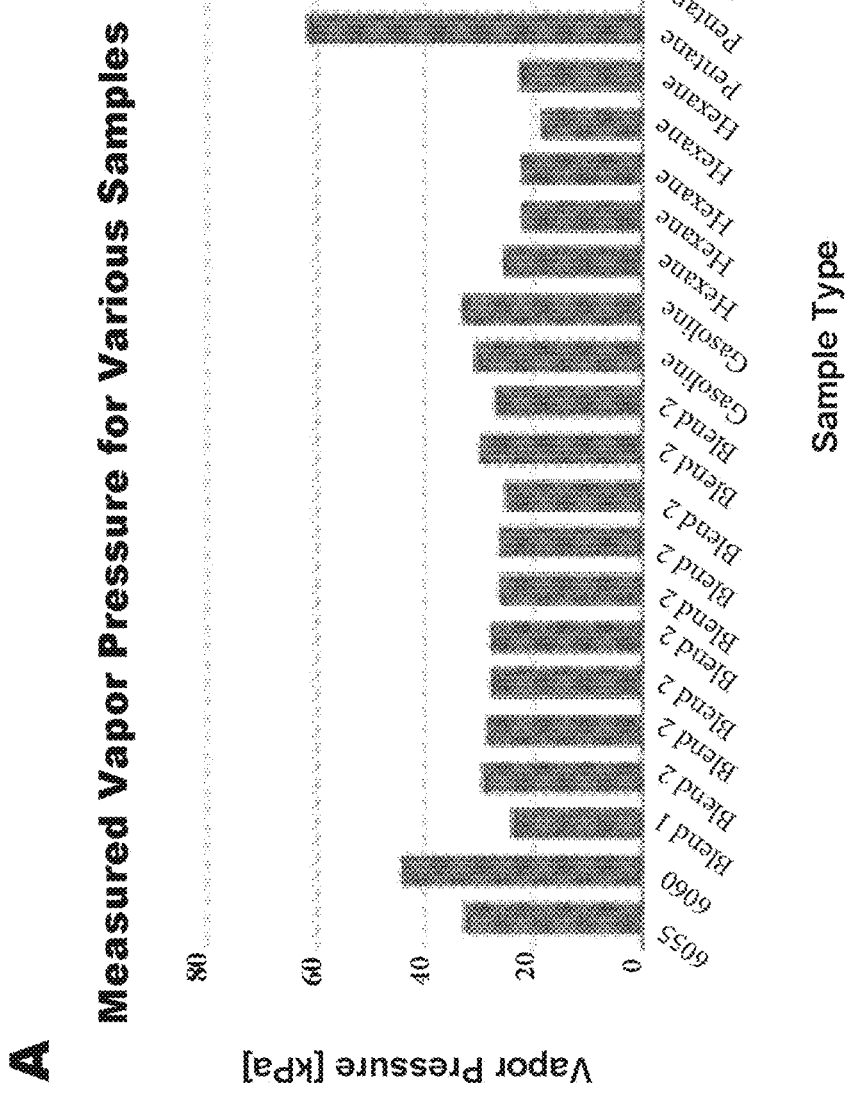
Figure 17 – (A) Aggregated vapour pressure measurements for various pure samples ranging from condensates (e.g. 6060), crude oil blends (e.g. blend 2) and pure alkanes (e.g. pentane).

Figure 17 – (A) (cont'd) Aggregated vapour pressure measurements for various pure samples ranging from condensates (e.g. 6060), crude oil blends (e.g. blend 2) and pure alkanes (e.g. pentane).

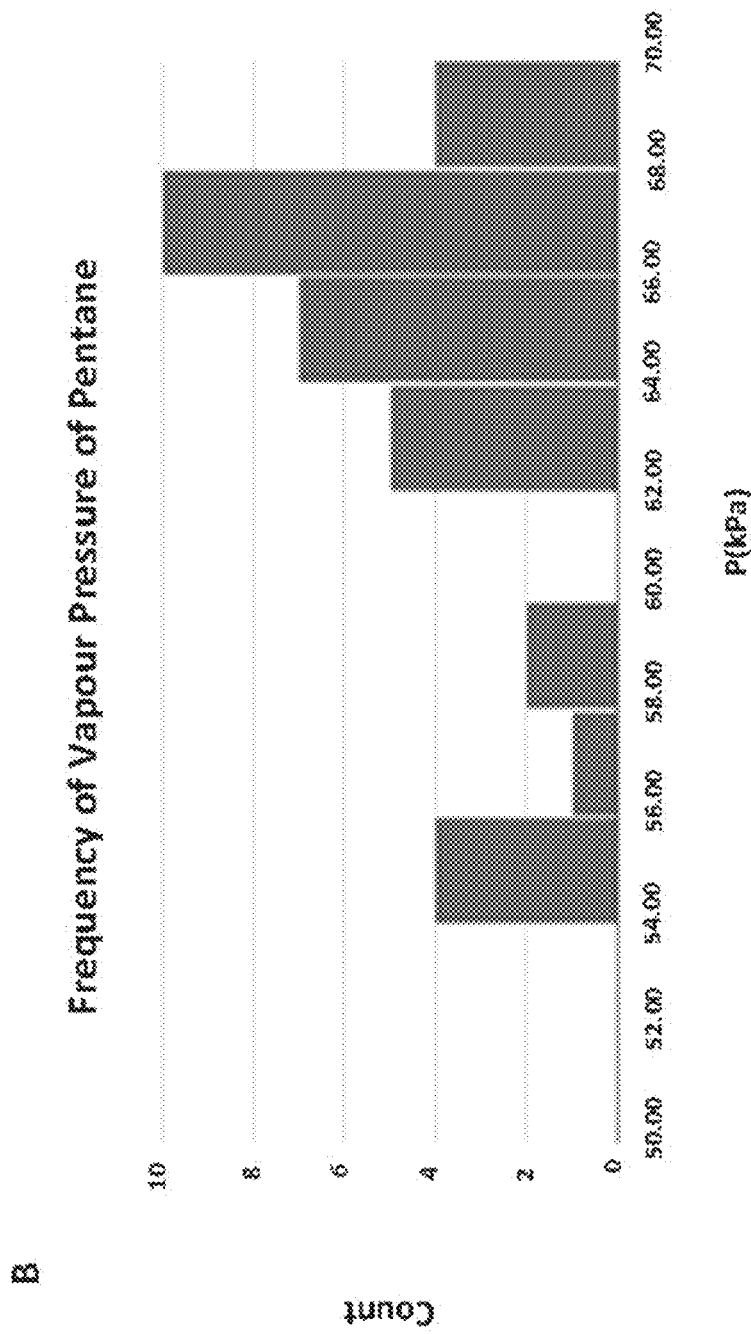
Figure 17 – (B) Distribution of repeated vapour pressure measurements of pentane.

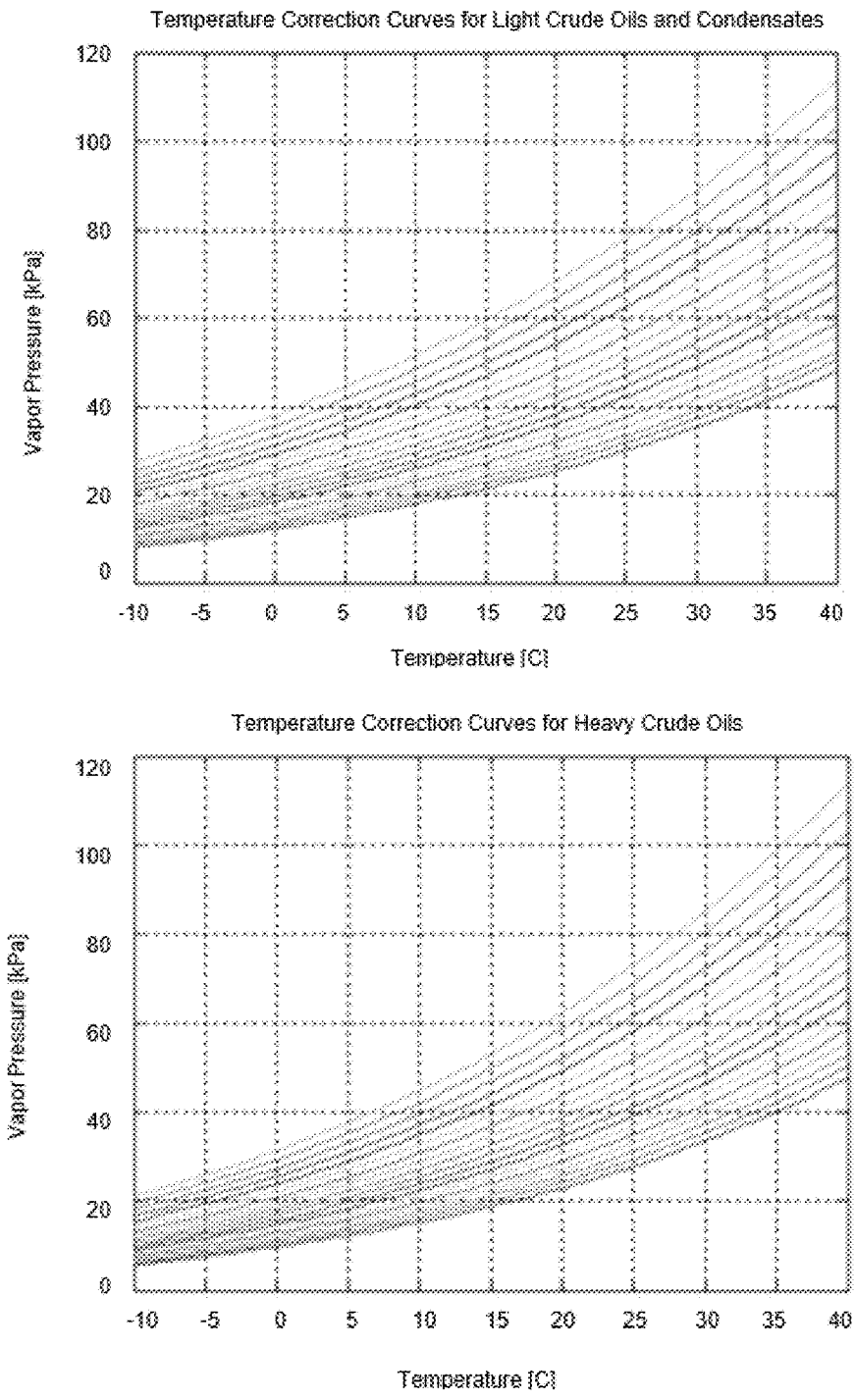

Figure 18 – In some embodiments, temperature correction is used instead of measurement temperature control. The use of real-time temperature correction mitigates the need to control temperature throughout the measurement process. Temperature correction curves for light and heavy crude oils (left, right respectively). This permits temperature extrapolation for comparison to industrial standard tests (i.e. vapour pressure at 37.8 C/100 F).

A
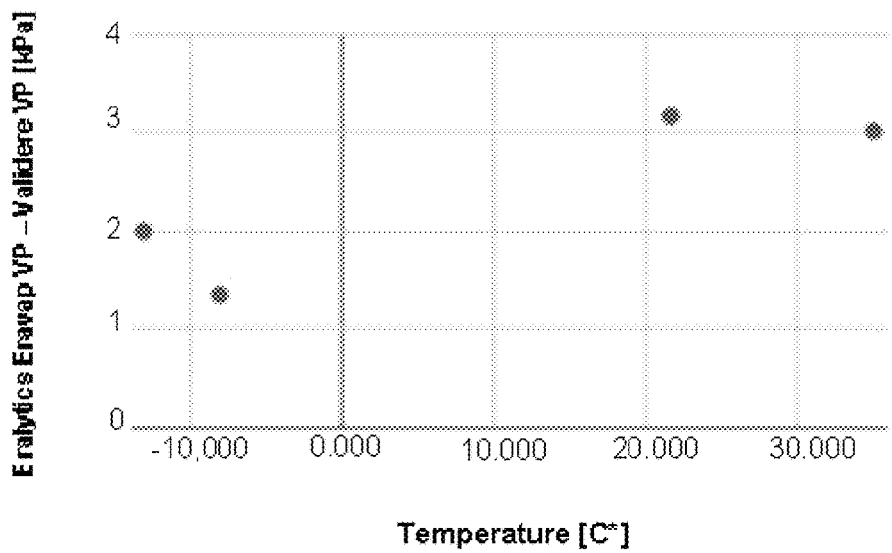
B
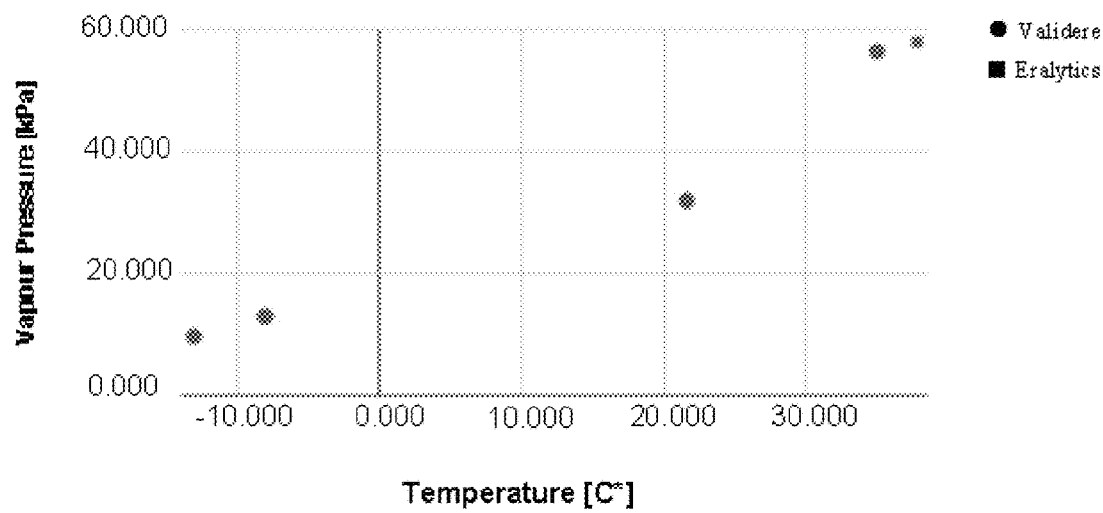
Figure 19 – (A) The difference of temperature corrected vapour pressure measurements of a condensate at select experimental temperatures and reference vapour pressure measurements via an Eralytics Eravap. (B) Uncorrected vapour pressure measurements at select experimental temperatures.

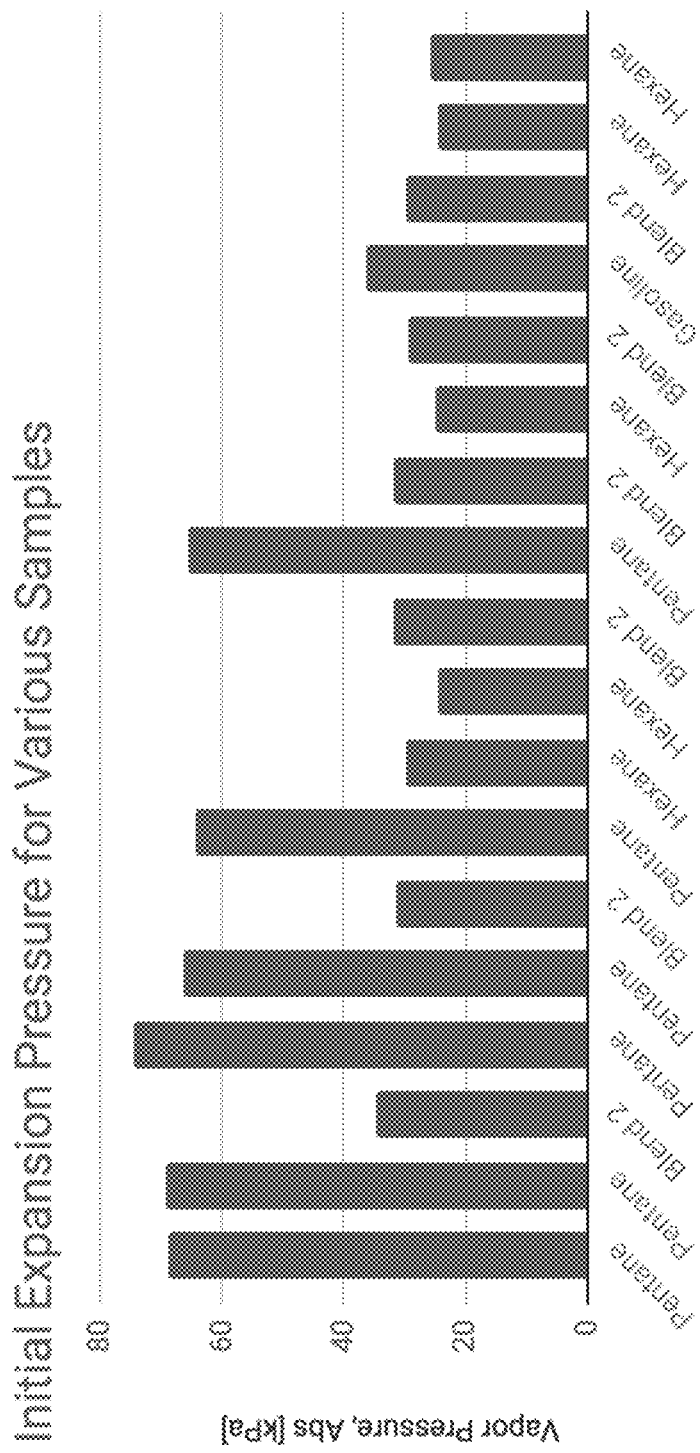
Figure 20 – In some embodiments, the sample chamber can be cleaned and reused. Above are sequential vapour pressure measurements with alternating alkanes/samples with known vapour pressures and crude oil blends. Cleaning with a specialized cleaning protocol was done between each test to ensure there was no cross sample contamination.

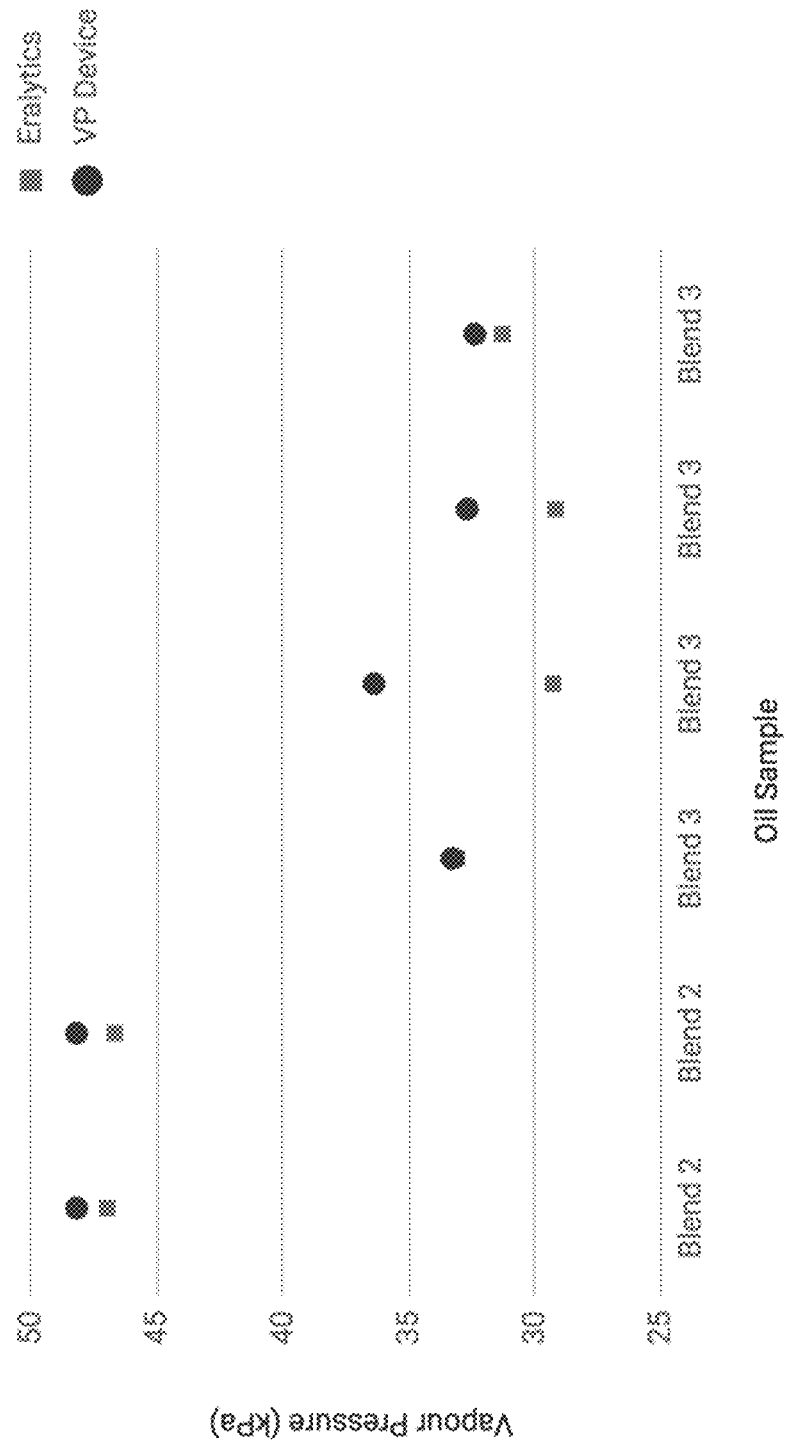

Figure 21 – Two crude oil blends were tested for vapour pressure in an alternating pattern and the intra-sample consistency is observed. This tested both repeatability of the measurement system, the cleaning protocol and its effectiveness in mitigating cross sample contamination. These temperature corrected measurements were compared to vapour pressure measurements obtained from a reference instrument (Eralytics Eravap) at 37.8 C.

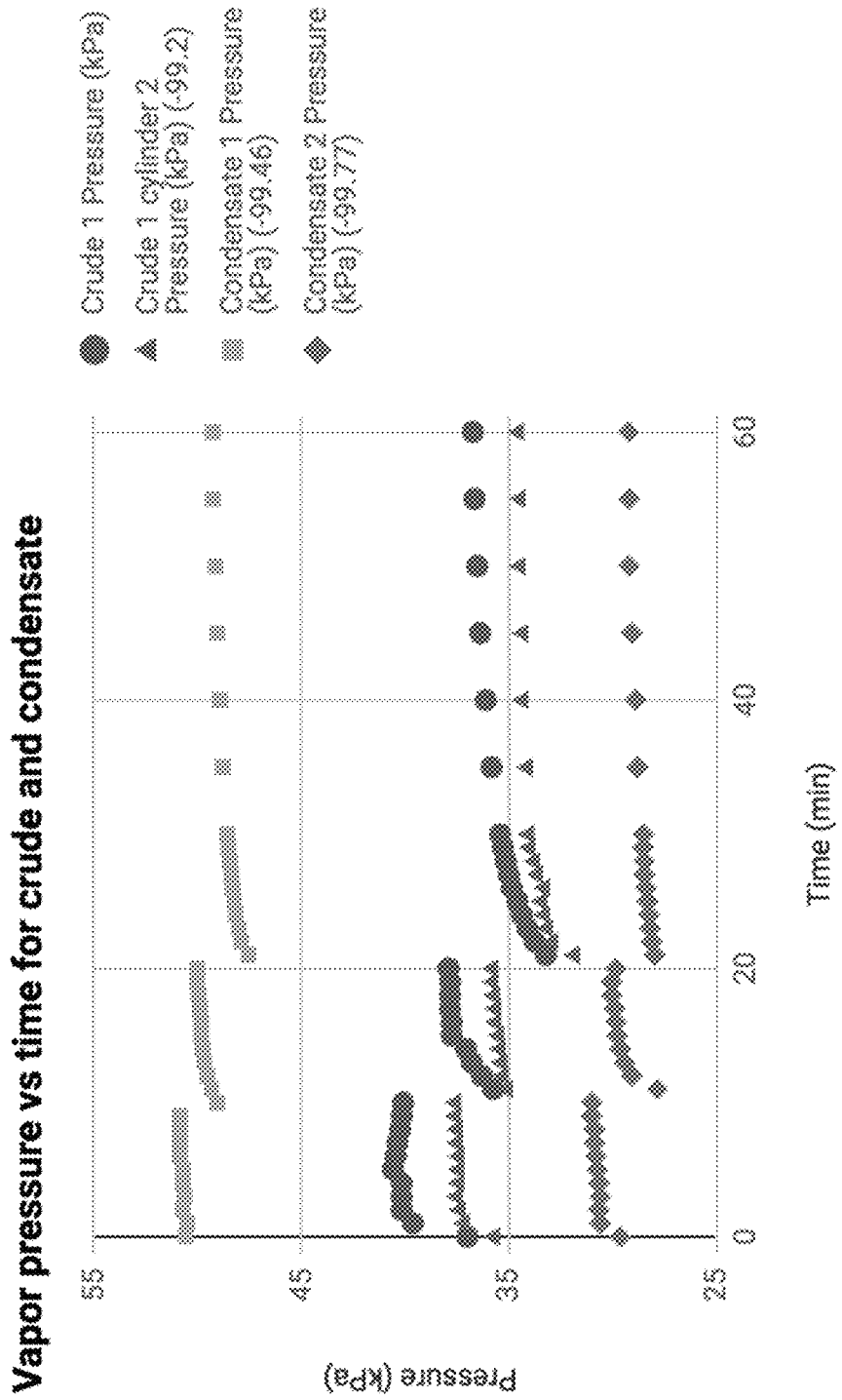
Figure 22 – In some embodiments, there are multiple measurement chambers with variable volumes allowing for multiple vapour expansions. Above are continuous pressure readings of various crude blends and condensates while undergoing a triple expansion measurement protocol (expansions occurring at 0, 10 and 20 minutes).

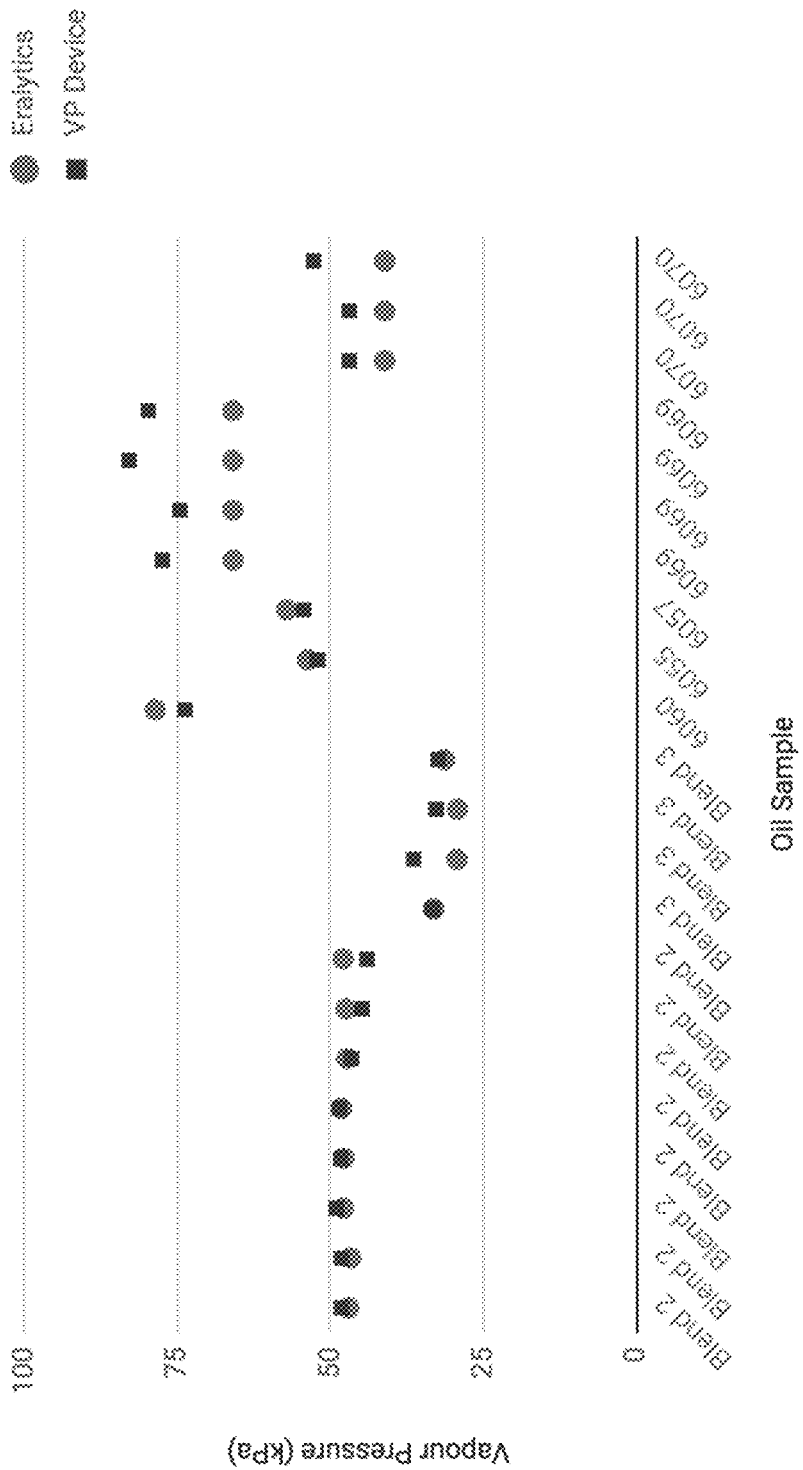

Figure 23 – In some embodiments, real time temperature correction is performed to relate measurements taken at experimental temperatures to sample vapour pressure at desired temperatures (typically 37.8 C). Above are temperature corrected vapour measurements obtained using the measurement apparatus (VP device) and the vapour pressure measurements obtained at the desired temperature 37.8 C via a reference instrument (Eralytics Eravap) for comparison purposes.

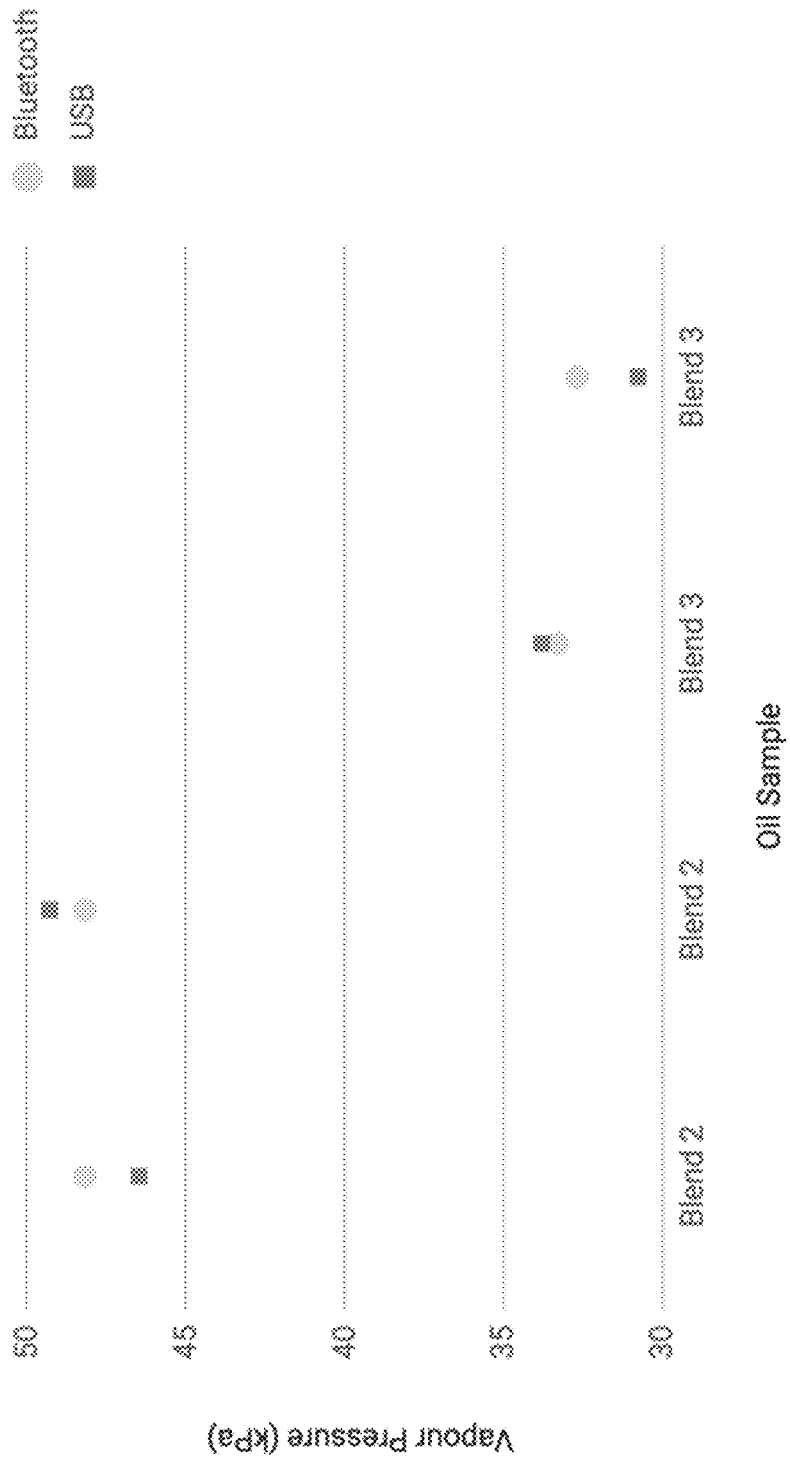

Figure 24 – According to the specifications of various embodiments, the measurement apparatus can make use of either a wireless Bluetooth pressure transducer or a wired USB pressure transducer for continuous vapour pressure measurements of the measurement chamber. Above are comparisons of vapour pressure measurements after temperature correction for both sensor types for different crude blends.

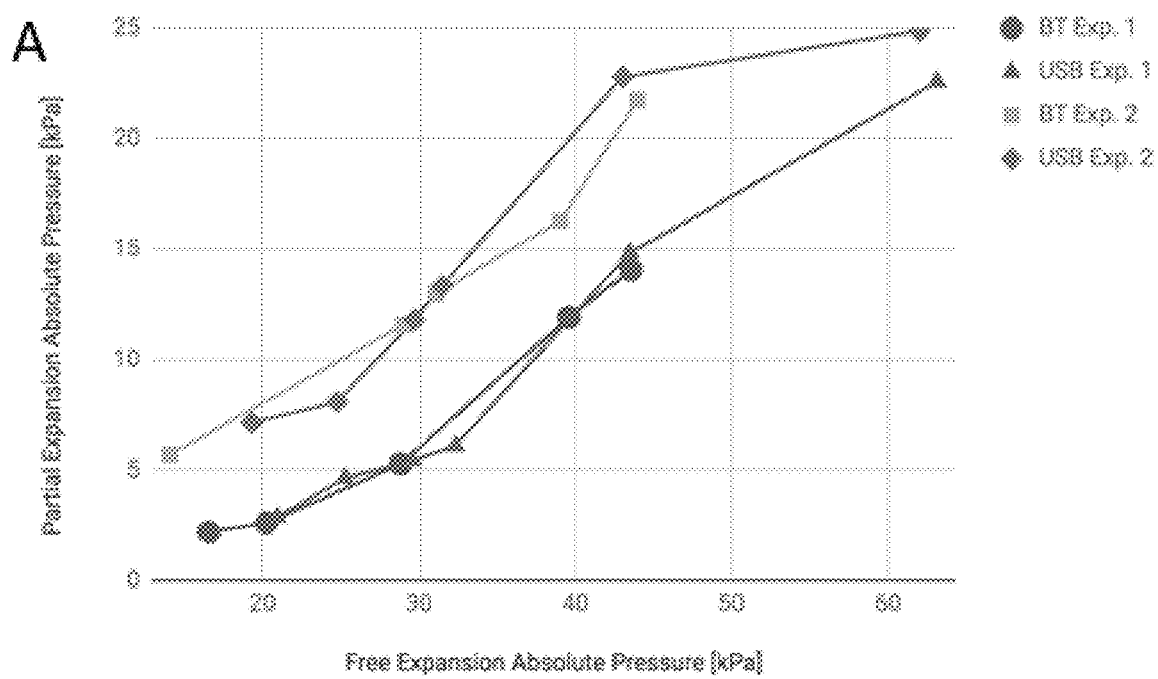

Figure 25 – In some embodiments, the measurement chamber is maintained at atmospheric pressures instead of either being completely evacuated, or filled with an inert gas. This mitigates the need for a vacuum apparatus at the experimental site. A partial vacuum is established upon connection of the sample and measurement chambers. This is denoted as a 'partial pressure expansion' compared to other embodiments where the measurement chamber is completely evacuated - denoted as 'a free expansion'. (A) There is a strong agreement over repeated tests for different sensor types (BT: bluetooth and USB) when comparing samples with various free expansion pressures and their corresponding partial expansion pressure.

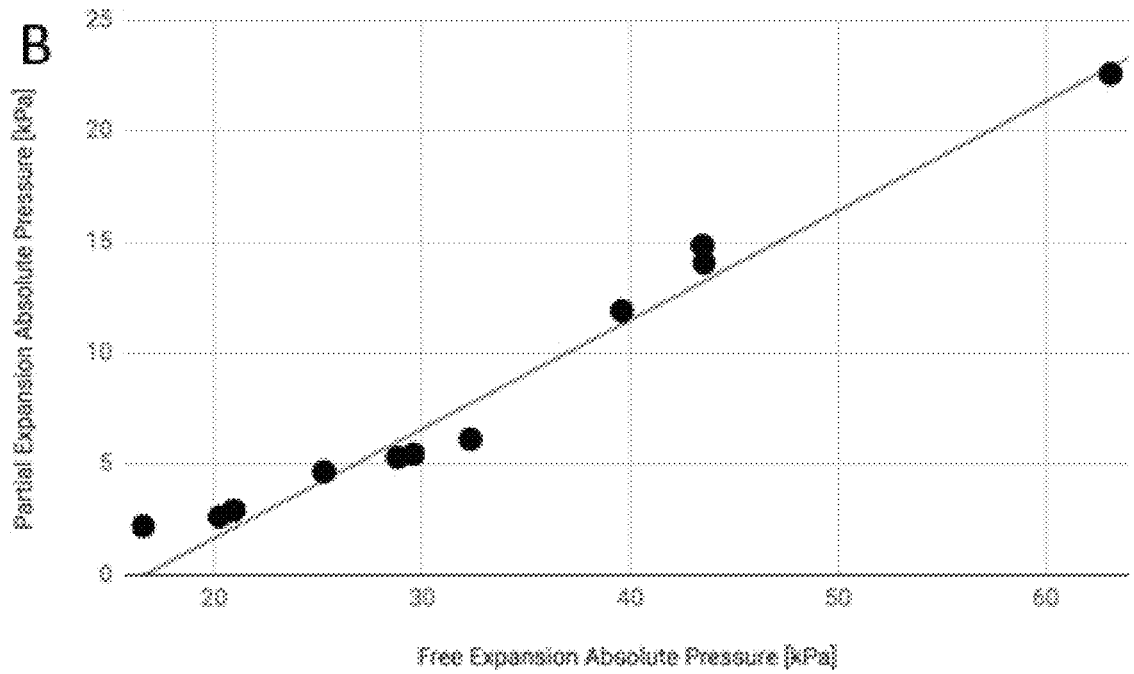

Figure 25 – In some embodiments, the measurement chamber is maintained at atmospheric pressures instead of either being completely evacuated, or filled with an inert gas. This mitigates the need for a vacuum apparatus at the experimental site. A partial vacuum is established upon connection of the sample and measurement chambers. This is denoted as a 'partial pressure expansion' compared to other embodiments where the measurement chamber is completely evacuated - denoted as 'a free expansion'. (B) There is a strong correlation between free expansion vapour pressure and the measured partial expansion vapour pressure ($R^2 = 0.986$).

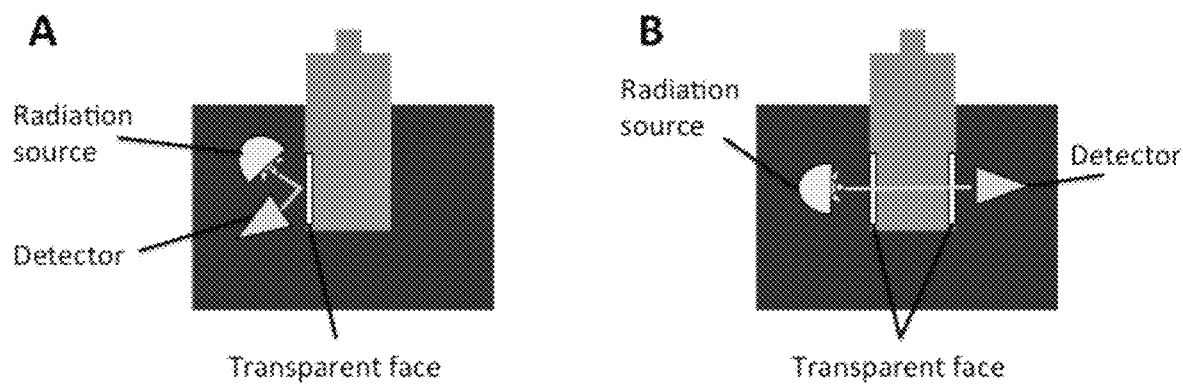

Figure 26 – In some embodiments, the reader contains at least one source of radiation and a detector and the sample container has at least one face that is transparent to the radiation. (A) In some embodiments, the source and detector are configured such that the detector detects scattered or reflected radiation. (B) In some embodiments, the detector detects transmitted radiation.

LIQUID TESTING SYSTEM AND METHOD

CROSS REFERENCE TO RELATED APPLICATIONS

This application is the national phase application of International Application No. PCT/CA2018/050167 filed on Feb. 14, 2018, which claims priority to and the benefit of U.S. Provisional Application No. 62/458,728 filed on Feb. 14, 2017, and U.S. Provisional Application No. 62/588,842 filed on Nov. 20, 2017, the entire contents of which are incorporated herein by reference.

FIELD

The present application pertains to the field of liquid analysis. More particularly, the present application relates to a portable system and method for the characterization of physical and chemical properties of liquids, in particular petroleum or petroleum liquids.

BACKGROUND

Several devices exist to characterize properties of liquids, such as petroleum and petroleum products, including density, vapour pressure, sulphur content, water and sediment content, viscosity and refractive index. However, users of these devices face numerous challenges for effective operation in the field. These devices do not feature effective integration between the sampling and measurement devices. Importantly, all of such devices typically require a sample preparation step that transfers liquid from a sampling container to the measuring device. This sample preparation step can introduce errors, and limits the overall accuracy of a measurement device to the care with which the operator has taken in the sampling step. As a result, only skilled operators can produce accurate measurements. Furthermore, sample preparation steps required in existing field instruments alter the integrity of the sample (e.g. by exposure to air during aliquoting, allowing light ends to evaporate and gas to dissolve) and therefore prevent samples from being easily stored for future testing in the event of a dispute or audit.

For example, any process during sampling or sample transfer that alters the external pressure on the liquid may also cause light fractions to phase separate and, therefore, may compromise the uniformity of the sample. Additionally, any sample transfer process that exposes the sample to the outside air could enable the contamination of the sample with air components (nitrogen, carbon dioxide, oxygen, water, etc.). These components can interfere with a number of measurements. Current testing methods that process pressurized samples require transfer of the samples under pressure to the testing apparatus. This transfer is done either through the use of pressurized piston cylinders (e.g. floating piston cylinders or manual piston cylinders) to take the sample and transfer it into measuring equipment, or require back pressure a pressurized source of immiscible fluid (e.g. water or ethylene glycol) to push the sample into the measurement instrument under a maintained elevated pressure. Pressurized piston cylinders are large, heavy, expensive and very difficult to use because they require extensive cleaning and recharging with pressurized gas between every measurement. Pressurized transfer of liquid using back pressure from a fluid also requires significant heavy equipment and highly skilled operators to execute. Both techniques are incompatible with practical frequent field use.

There is a pressing need for a portable device that integrates representative sampling and accurate measurement into a single process, particularly one that does not require skilled operators or external sample manipulation in the field. There is also a pressing need for field testing equipment that is capable of performing non-destructive quality analysis on petroleum products.

This background information is provided for the purpose of making known information believed by the applicant to be of possible relevance to the present invention. No admission is necessarily intended, nor should be construed, that any of the preceding information constitutes prior art against the present invention.

SUMMARY

An object of the present invention is to provide an improved method and portable system for the characterization of properties of liquids, particularly petroleum and petroleum liquids In accordance with an aspect of the present application, there is provided a method of analyzing a sample directly in a container, comprising the steps of: providing a container; obtaining a sample to be analyzed in the container, the sample being obtained from a sample source; performing one or more measurements on the sample directly in the container with a reader; and visually outputting the one or more measurements to a device. The sample can be a petroleum or petroleum liquid sample.

Ideally, the sample may be measured directly in the container without removal of sample from the container, such that the sample is not exposed to an external environment to the container.

The present method may be used to obtain information on quality, price, authenticity, adherence to certain industry standards (e.g. pipeline or refinery specifications) or government regulations. The one or more measurements may comprise, for example, weighing the sample, density or specific gravity, vapour pressure, sulphur content, water content, viscosity, colour, and/or refractive index.

The density of the sample may be determined independent of the temperature at the time of measurement. Ideally, the density may depend on the temperature at the time of sampling.

The sampling source may be, for example, a pipeline, storage tank, tanker truck, or rail car.

In certain embodiments, two or more of the containers are positioned in an array, wherein each of the two or more containers are fluidly connected with each other. The sample may be provided in each of the two or more containers, such that the sample is capable of being analyzed in each of the two or more containers. There may be a further step of performing a replicate analysis of the sample in each of the two or more containers, or a further step of performing a unique analysis of the sample in each of the two or more containers.

The one or more measurements may comprise determining the vapour pressure of the sample. In this embodiment, the sample may be obtained from the sample source at the pressure of the source, wherein the pressure of the sample is maintained during transport and/or testing of the sample.

In certain embodiments, the container is in communication with one or more other containers via a central processing unit (CPU). The CPU may be a cloud server which connects the one or more containers through the internet. The CPU may communicate with one or more readers connected to one or more containers, or the CPU may communicate through a local connection, such as a network cable, USB connectivity, Bluetooth or Wifi, for example. In some embodiments, the CPU may be integral with one or more of the containers, one or more readers, or both.

The one or more of the containers and/or one or more of the readers may comprise a processor for processing the one or more measurements to obtained processed data. The measurements obtained from the sample may be analyzed by external processors to obtain processed data. The processed data may be in communication with an external device, such as a mobile device or smartphone, to display the processed data on a screen thereof.

In accordance with another aspect, there is provided a method of analyzing a petroleum sample directly in a container, such that the sample is not exposed to an environment external to the container, comprising the steps of: providing a container; obtaining a sample to be analyzed in the container, the sample being obtained from a sample source; performing one or more measurements on the sample directly in the container with an reader; and outputting the one or more measurements to a visual device.

In accordance with another aspect, there is provided a system for analyzing a sample directly in a container, the system comprising: one or more sample containers for storing a sample to be analyzed, the sample being obtained from a sample source; and one or more sample readers for directly analyzing the sample in the one or more sample containers to provide one or more measurements of the sample. The system may further comprise a reader for visualizing the one or more measurements.

In certain embodiments, the system may comprise two or more sample containers. The two or more sample containers may be fluidly connected to each other. In certain embodiments, the sample may be capable of being analyzed in each of the two or more containers. A processor may further be part of the system. The system may be used to obtain one or more measurements as described herein.

The one or more sample containers in the system may be in communication with one or more other containers via a central processing unit (CPU). The CPU may be a cloud server which connects the one or more containers through the internet. The CPU may communicate through a local connection, such as a network cable, Bluetooth or Wifi, for example. The CPU may be integral with one or more of the containers, one or more readers, or both. The one or more of the containers and/or one or more of the readers may comprise a processor for processing the one or more measurements to obtained processed data. The measurements obtained from the sample may be analyzed by external processors to obtain processed data. The processed data may be in communication with an external device, such as a mobile device or smartphone, to display the processed data on a screen thereof.

In another aspect, there is provided a method of measuring vapour pressure in a sample obtained directly from a sample source, the method comprising: obtaining a sample from a sample source; and exposing the sample to a vapour chamber with a pressure transducer to measure vapour pressure.

The present application describes a portable system that performs quality tests on petroleum products without requiring any sample preparation or handling. In certain embodiments, the system typically comprises two main components as illustrated in FIG. 1: a sample container, and a reader. In certain embodiments, the sample container is capable of connecting directly to a sampling point on a pipeline, storage tank, tanker truck, or rail car. In order to make a measurement, the sample container, filled with the liquid, is connected to the reader. The reader makes the measurement without requiring a transfer of the sample that would expose the sample to the outside environment. In certain embodiments, the sample container may be releasably fixed to the vessel over long times (e.g. one week, one month, one year, etc.) and draws a composite sample from the vessel, designed to be representative of a longer time-period. In these embodiments, the sample container is removed from the vessel only to test at the end of the sampling period. In certain embodiments, the sample container is permanently affixed to the vessel and is used to draw sample and test it on demand. In these embodiments, the reader is releasably attachable and is attached to the sample container only when a measurement is being made.

In certain embodiments, the sample container comprises an array of detachable containers as illustrated in FIG. 2A. Each container can comprise valves at connection points such that samples can be isolated from one another when the containers are detached from a source or from one another. Each container can be connected to the sampling point individually and filled separately or connected in series in multiple chambers (such as in an array) in any combination and filled together. These multiple chambers can be designed such that each may conduct different types of tests, or to enable replicate sampling and measurements of the same test or tests.

In certain embodiments, the sample container or container array takes a liquid sample using a 'flow-through' technique from a pressurized source (e.g. pipeline, large tank), where sample flows through the container at the source pressure for a certain time before valves at either end of the sample container are closed, maintaining the source pressure inside the container during transport and testing of the sample (FIG. 2B). In some embodiments, the reader may comprise one unit that connects to multiple containers and conducts multiple tests (FIG. 3A). In some embodiments, the reader may comprise an array of units, each connecting to one or more sample container types and performing one or more different tests (FIG. 3B). In some embodiments, the individual units in an array may communicate with one another via a central processing unit (CPU), such as a cloud server, connected to the array through the internet. The CPU may be located near the array and communicate with the reader units through local connections (e.g. network cable, Bluetooth, WiFi, etc.). Optionally, the CPU for all units in the array may be incorporated into one of the units. At least a part of the data analysis may be performed by the on-board processor (e.g. conversion of the optical readings to liquid property data) and a part of the data analysis may be performed by external processors (e.g. comparison with external libraries). Some parts of the processed data may be shared with apps on the user's other mobile devices (e.g. smartphones).

Thus, in one aspect, there is provided a method of analyzing a petroleum sample directly in a container, such that the sample is not exposed to an environment external to the container, comprising the steps of: (a) providing a container, the container comprising: a sample chamber capable of being fluidly connected to a sample source for flow-through sampling, and a measurement chamber, wherein the measurement chamber is capable of being fluidly connected to the sample chamber, the sample chamber comprising: an inlet valve and an outlet valve for flow-through sampling of the petroleum sample, a measurement valve for releasing the sample to the measurement chamber, and an inline filtering component disposed between the measurement valve and a point of connection of the sample chamber to the measurement chamber, the measurement chamber comprising: at least a first chamber fluidly connected to one or more sensors for measuring pressure and temperature, and a closure valve; (b) connecting the sample chamber to the sample source; (c) allowing the sample to flow from the sample source through the sample chamber via the inlet valve and the outlet valve, and thereafter closing the inlet valve and the outlet valve to obtain the sample to be analyzed in the sample chamber; (d) connecting the sample chamber to the measurement chamber; (e) moving the measurement valve to an open position to release the sample to the measurement chamber, wherein sample liquid is contained by the inline filtering component and wherein sample vapour enters and expands within the first chamber of the measurement chamber; and (f) measuring the pressure and temperature of the sample vapour in the measurement chamber.

In one embodiment, the sample chamber can be connected to the measurement chamber prior to step (c) of allowing the sample to flow from the sample source through the sample chamber and obtaining the sample to be analyzed in the sample chamber.

In another embodiment, the measurement chamber is fluidly connected to the sample chamber via a releasable connection.

In yet another embodiment, the step of measuring the pressure and temperature of the sample vapour in the measurement chamber occurs after the sample vapour expansion has reached equilibrium; optionally, the method further comprising a step of reporting the equilibrium vapor pressure of the sample to a user.

In still yet another embodiment, the method further comprises a step of reporting the equilibrium vapor pressure of the sample to a user, either at the temperature in the vapor chamber or at another reference temperature, wherein the step of reporting occurs prior to the sample vapour expansion reaching equilibrium, and an extrapolation algorithm is used to predict the equilibration vapour pressure based on elapsed expansion time and the time variation of the pressure and temperature measurements. In another embodiment, the extrapolation algorithm to predict equilibrium vapor pressure from the time-varying pressure and temperature measurements incorporates statistical correlations to a library of previous measurements in the container that were allowed to reach equilibrium.

In still yet another embodiment, the closure valve of the above-noted measurement chamber is fluidly connected to a vacuum apparatus, and the measurement chamber is evacuated and subject to a vacuum prior to each sample measurement. In another embodiment, the measurement chamber is pressurized with an inert gas following evacuation, prior to each sample measurement. In still yet another embodiment, the measurement chamber is maintained at atmospheric pressure prior to each sample measurement, and an algorithm is used to predict a free expansion vapour pressure of the sample vapour based on a measured partial expansion pressure of the sample vapour.

In another embodiment, the above-noted container for measuring the pressure and temperature of sample vapour from a petroleum sample can be fluidly connected to one or more additional containers configured to measure one or more additional properties of the sample (such as sample weight, density or specific gravity, sulphur content, water content, viscosity, colour, and/or refractive index), the method further comprising: connecting the container to one or more additional containers configured to measure one or more additional properties of the sample, and measuring one or more additional properties of the sample.

In an alternate embodiment, the container comprises a sample container and a measurement container that are formed as a unitary structure.

In some embodiments, the system reports information to the user via a screen incorporated into the reader. The reported information may be stored on an external server. This information may be accessible to the user via internet login, mobile apps, etc. Typically, the reported information from the system can include raw measurements, quality, price, authenticity, adherence to certain industry standards (e.g. pipeline or refinery specifications) or government regulations. In some embodiments, the information measured by this testing system may include density or specific gravity, vapour pressure, sulphur content, water content, viscosity, colour and refractive index.

In certain embodiments, the device may be used to characterize crude oil or refined petroleum products.

BRIEF DESCRIPTION OF THE FIGURES

For a better understanding of the present invention, as well as other aspects and further features thereof, reference is made to the following description which is to be used in conjunction with the accompanying drawings, where:

FIG. 1 provides a general schematic of an overall concept as described herein.

FIGS. 2A and B provide exemplary schematics showing a sample container array.

FIGS. 3A and B provide schematics of different reader configurations for a sample chamber array.

FIGS. 4A and B provide different embodiments of a sample container which may be used in the context of the present application.

FIG. 5A-C provide exemplary schematics of density measurement in a container.

FIG. 6 illustrates density of water measured at different sampling temperatures using the embodiment of FIG. 5.

FIG. 7 illustrates (A) general schematic of vapour pressure measurement and (B) a schematic of apparatus which may be used in the context of the present application.

FIGS. 8A and B provide schematics of a liquid chamber being filled using a flow-through technique from a pressurized pipeline flow.

FIGS. 9A and B illustrate exemplary configurations of liquid and vapour chambers.

FIGS. 10A and B illustrate one or several measurement valves.

FIGS. 11A and B provide schematics of the measurement chamber, sample chamber and vacuum apparatus configuration.

FIGS. 13A, B and C illustrates the decrease of vapour pressure for various sample types when left exposed to the atmosphere for extended durations.

FIGS. 14A and B illustrate the measured vapour pressure of pentane in comparison to standard pentane vapour pressures.

FIGS. 15A and B illustrates vapour pressure measurements of acetone and hexane at various controlled experimental temperatures in comparison with standard acetone and hexane temperature curves.

FIG. 16 illustrates (A) vapour pressure measurements for various pure alkanes and a (B) a constructed temperature-vapour pressure curve for octane.

FIG. 17 illustrates (A) an aggregated set of vapour pressure measurements for crude oil blends, condensates and pure alkanes. (B) illustrates the distribution of repeated pentane vapour pressure measurements.

FIG. 18 illustrates temperature correction curves for light and heavy crude oils.

FIG. 19 illustrates (A) accuracy of the temperature corrected vapour pressure measurements of a condensate at various experimental temperatures and (B) a constructed vapour pressure-temperature curve.

FIG. 20 illustrates sequential and alternating measurements of crude oils and pure alkanes to test measurement repeatability and the possibility of cross sample contamination post cleaning.

FIG. 21 illustrates sequential and alternating measurements of crude oils and comparisons to a reference instrument to test for cross sample contamination after cleaning.

FIG. 22 illustrates continuous vapour pressure measurements for various light crude oils and condensates over the duration of a triple expansion measurement.

FIG. 23 illustrates temperature corrected vapour pressure measurements made by the measurement apparatus in comparison to vapour pressures obtained using a reference instrument.

FIG. 24 illustrates the comparable temperature corrected vapour pressure measurements for select crude oil blends while using different pressure transducers (i.e. bluetooth vs USB).

FIGS. 25A and B illustrate vapour pressure results from another embodiment where the measurement chamber is maintained at atmospheric conditions.

FIGS. 26A and B illustrate embodiments of the reader and sample container.

DETAILED DESCRIPTION

Figure 12A:
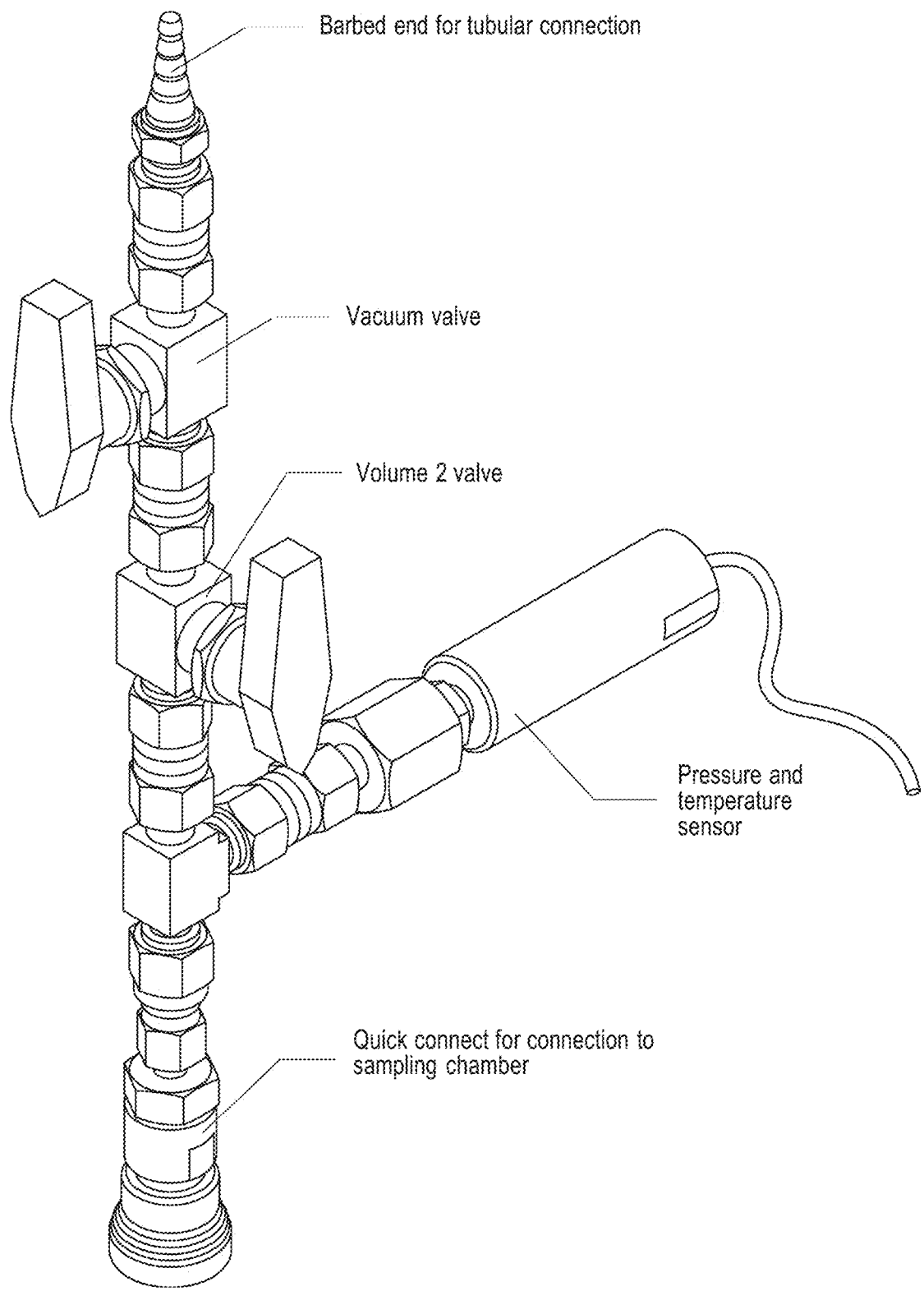
FIGS. 12A and B provide a detailed schematic of a single embodiment of components used in the measurement and sample chambers.

Unless defined otherwise, all technical and scientific terms used herein have the same meaning as commonly understood by one of ordinary skill in the art to which this invention belongs.

As used in the specification and claims, the singular forms "a", "an" and "the" include plural references unless the context clearly dictates otherwise.

The term "comprising" as used herein will be understood to mean that the list following is non-exhaustive and may or may not include any other additional suitable items, for example one or more further feature(s), component(s) and/or ingredient(s) as appropriate.

FIG. 1 provides an exemplary schematic of one embodiment of a system as described herein. A sample container collects the sample and then is connected to a reader. The reader performs a measurement on the sample without requiring the transfer of any liquid from the sample container.

To gain a better understanding of the invention described herein, the following examples are set forth. It should be understood that these examples are for illustrative purposes only. Therefore, they should not limit the scope of this invention in any way.

1. Sample Container

The same sample container may be used to draw the sample directly from a source (e.g. pipeline, tank, etc.), store the sample during transport and then connect directly into a reader that makes the measurement. Thus, in one embodiment, the sample container may also be considered the measurement chamber. Sampling techniques used for most petroleum characterization instruments today require transfer of liquid from the sampling container to the measurement chamber, a transfer process that is prone to operator error. However, in accordance with the method and system as described herein, one sample container may be used as the measurement chamber for all measurements.

FIG. 2A illustrates one example where a sample container comprises an array of detachable containers, wherein each container comprises valves at connection points so that samples can be isolated from one another when the containers are detached from a source or from one another. In this arrangement, each container may be connected to the sampling point individually and filled separately or connected in series in any combination and filled together. These multiple chambers may be designed such that each conducts different types of tests, or to enable replicate sampling and measurements of the same test or tests. In certain applications of certain embodiments, one or more of the sample chambers may be stored as a physical record for later analysis. Ideally, one or more sample containers in an array are DOT-compliant sample cylinders that can used to transport petroleum samples to centralized lab facilities. FIG. 2B illustrates that sampling can be done in all chambers together using a flow-through method.

In some embodiments, the sample container or array has a valve or cap at one end and is filled via decantation (FIG. 4A). FIG. 4B illustrates an embodiment where the sample container is capped with a valve, cap or seal at two ends to enable flow-through sampling. The sample container or array may contain valves or seals at two ends and liquid sample is drawn into the container using a 'flow-through' technique from a pressurized source of liquid (e.g. pipeline, large tank). In the flow-through technique, the sample container is connected in-line with the pressurized source, and sample is allowed to flow through the container in one direction for a certain amount of time. After the steady flow is achieved for enough time to ensure a representative sample, the valves on either end are closed, preserving the sample inside under the same pressure conditions as the source. Crude and refined petroleum products are complex mixtures that may contain highly volatile fractions or dissolved gases. Therefore, many types of measurements (e.g. vapor pressure, compositional analysis, etc.) require sample pressure to be preserved in order to obtain an accurate result.

2a. Density Measurement

A testing device or reader for use in accordance the method and system as described herein may, for example, measure density of the fluid. The density of the fluid may be measured inside the sample container. In some embodiments, the reader contains a device capable of measuring the mass of the sample container containing the liquid, such as a load cell or a strain gauge. In these embodiments, as illustrated in FIG. 5, the sample container is connected to the reader such that the weight of the sample container, completely filled with liquid, is supported by the load cell or strain gauge and the mass of the sample container is recorded. The density of the liquid is calculated from the mass of the liquid. Having the liquid completely fill the container ensures a fixed and known volume of liquid is used to calculate density. The accuracy of the density calculation is typically limited by: 1) the uncertainty in the mass of the sample container; 2) the uncertainty in the volume of the liquid in the sample container, including any liquid residue on the inlet or outlet, and/or 3) the measurement accuracy and calibration of the load cell or strain gauge. It would be known to those skilled in the art that the density of a liquid varies with temperature. In this example, the reader directly measures only the mass of the filled sample container, which is filled with liquid under the pressure of the sample source (e.g. pipeline, tank). Therefore, the temperature relevant for the density determination was that at which the sample was collected from the pressurized vessel (e.g. pipeline, tank, rail car, truck, etc.) into the sample container. After sampling from the vessel, once the sample container is sealed, the total mass of the sample container and the liquid it contains does not change with temperature. Therefore, the mass can typically be measured at any ambient condition in the future and the density can be calculated still only based on the known temperature inside the sample source vessel (e.g. pipeline), since no mass leaves the pressurized container at any temperature and pressure after taking the sample. This design presents a significant advantage over existing technologies when measuring density in remote locations because it does not require the temperature to be controlled during measurement.

FIG. 5 thus illustrates an exemplary schematic of density measurement according to certain embodiments. A sample container completely filled with liquid (FIG. 5A) is placed on an apparatus containing a load cell or strain gauge (FIG. 5B) that measures its mass. The sample container can also be weighed in a hanging configuration (FIG. 5C). Since the sample container is filled at the temperature of the source, measuring the mass of the filled container under any conditions allows the instrument to calculate the density at the temperature of the source. This removes the requirement to control or monitor temperature during measurement.

FIG. 6 illustrates the density of deionized water measured according to the example illustrated in FIG. 5, with sampling done at different temperatures between 25° C. and 40° C. All mass measurements were taken at room temperature (20° C.). Within the error of the load cell (1 g/L), all measurements agree with reference values corresponding to the temperature recorded during sampling, and vary independently of the temperature recorded during measurement. As shown, density follows the temperature of sampling, as predicted.

Where a CPU is used, the CPU uses the density measurement at a known temperature (the temperature of the sample when drawn) to calculate the density of the liquid at other temperatures relevant to the user (e.g. industry standard reporting temperatures for density measurements). For most pure substances and simple mixtures, the density variation with temperature follows relationships that would be understood by those skilled in the art. For certain complex mixtures, the empirical relationship between density and temperature is made available in public databases. For example, the American Petroleum Institute and ASTM International publishes such data for crude oil.

2b. Vapor Pressure

In certain embodiments of the method and system as described herein, there may be provided a combination of sample container and reader that are configured to measure vapor pressure of a liquid. FIG. 7A shows a general schematic of vapour pressure measurement. FIG. 7B shows an exemplary schematic of a system according to certain embodiments. A liquid chamber with volume (Vl) contains two sampling valves at either end and is connected to a vapor chamber with volume (Vv) by a measurement valve. The vapour chamber contains a pressure transducer. In some embodiments, the vapour chamber also contains an evacuation valve that enables the atmosphere to be preset before a measurement (e.g. as vacuum, air, or another inert gas filled to a given pressure).

In this example, illustrated in FIG. 7A, vapor pressure is measured in a closed chamber with a fixed fraction of the chamber volume containing the liquid and the remaining fraction of the volume allowed to fill with vapor. There are several conditions that must be controlled or accounted for in a vapor pressure measurement: the ratio of the liquid to vapor in the chamber during the measurement (generally called the 'V/L ratio'), the temperature of the liquid and vapor inside the chamber, and the starting pressure of any gas (e.g. air, nitrogen, argon, helium, vacuum etc.) before the liquid is added. Additionally, while taking the sample and inserting it into the chamber, any steps that could alter the content of dissolved gases in the liquid, by either causing new gas to dissolve in the liquid or allowing volatile fractions of a liquid mixture to evaporate, must be controlled or accounted for. Dissolved gases are most commonly added to the sample when the sample is exposed to the outside air. In certain existing vapor pressure test methods (e.g. ASTM D323, D5191), air exposure is unavoidable and therefore a controlled air saturation step is included in the test method. However, exposure to air is highly undesirable in vapor pressure testing on certain petroleum products, crude oil in particular. Vapor pressure is frequently measured on crude oils, condensates, and natural gas liquids as a means to estimate the quantity of the lightest fractions (e.g. methane, ethane, propane, butane, hydrogen sulphide, etc.), several of which are gases at ambient pressures and temperatures. Therefore, exposure of the sample to air at any time during sampling or measurement typically has a particularly detrimental effect on the integrity of the vapor pressure measurement on these products. FIG. 13 illustrates the susceptibility of crude oils to be compromised after prolonged exposure to air. In the select samples, vapour pressure decreased by 14-28% over a 10 minute period of exposure. Adding dissolved air typically prevents accurate quantification of dissolved gases. Processes during sampling or sample transfer that alters the external pressure on the liquid may also cause light fractions to phase separate and therefore compromise the uniformity of the sample.

Current test apparatuses and test methods (e.g. D6377, D7975) on the market to properly measure the vapor pressure of crude petroleum products that may contain volatile fractions (e.g. crude oil, condensate, natural gas liquids) require the use of pressurize piston cylinders (e.g. floating piston cylinder or manual piston cylinders) to take the sample and transfer it into measuring equipment. These cylinders are large and very difficult to use because they require extensive cleaning and recharging with pressurized gas between every measurement. By contrast, the present application provides exemplary methods whereby the sample container and reader that measure vapor pressure, acquire a pressurized sample using a flow-through method and do not require any transfer of the sample afterward. Ideally, this may enable a much simpler measurement with fewer steps, without requiring pressurization with an inert gas between measurements.

FIG. 7B illustrates one exemplary apparatus that may be used in the context of the present method. In this configuration, a liquid chamber is enclosed by three valves. The two valves on either end enable sampling via a flow-through technique (as illustrated in FIG. 8) and the third valve connects the liquid and vapor-containing volumes during measurement. At the end of the vapor chamber is a pressure transducer, or pressure gauge. The chamber may also contain an additional valve that allows the chamber to be evacuated before measurement (as shown in FIG. 7B).

In one example, a sample is introduced into a liquid chamber of the container from a pressurized source (e.g. pipeline) using a flow-through technique. FIG. 8 illustrates one exemplary schematic of the liquid chamber being filled using a flow-through technique from a pressurized pipeline flow according to certain embodiments. This technique enables the sample to be taken with the pipeline pressure preserved and without being exposed to the outside air. In FIG. 8A, the sample flowing through the container is collected into a waste bucket. In FIG. 8B, the sample flowing through the container is returned to the pipeline. The flow-through technique illustrated in FIG. 8 enables samples to be taken with the pressure of the source maintained, without requiring the use of pressurized cylinders. Typically, the sample chamber may be evacuated before it is connected to the source. In other examples, the sample chamber may be air filled before it is connected to the source, or is filled with an inert gas before connecting to the source. In other examples, the sample chamber is filled with an incompressible fluid that is immiscible with the sample before the chamber is connected to the source (e.g. water, glycerol, ethylene glycol). In these examples, the immiscible liquid is displaced by the sample, preventing the sample from expanding or losing pressure as it fills the chamber. The flow of the pressurized sample from the source through the sample chamber may, in certain instances, be allowed to proceed for a certain time to enable equilibration of a representative sample before the valves are closed on both ends to lock in the sample.

FIG. 9 illustrates one configuration of the liquid and vapour chambers according to certain embodiments. In the embodiment shown in FIG. 9A, the liquid chamber is detached from the rest of the apparatus during sampling. In the embodiment shown in FIG. 9B, the liquid chamber and the vapour chamber remain connected during sampling.

As illustrated in FIG. 9A, the sample chamber and the vapor chamber (with the pressure transducer) may be disconnected during sampling. After the sample is collected, the sample chamber is connected to the vapor chamber. The vapor chamber may then be evacuated or purged with inert gas through the evacuation valve before the measurement valve is opened, exposing the vapor chamber to the liquid and allowing the vapor pressure to build. Optionally, the vapor chamber may remain connected to the sample chamber during sampling. In these embodiments, the evacuation or purging of the vapor chamber can be done before or after the sample is taken, as long as it is done before the measurement valve is opened.

The V/L ratio is controlled by the volume ratio between the vapor chamber (Vv) and the sample chamber (Vl). In using the method as described herein, different sized vapor chambers may be connected to the sample chamber to measure the vapor pressure at different V/L ratios. One or more extra valves may be added within the vapor chamber or several vapor chambers may be connected in series to enable the vapor pressure to be measured with multiple V/L ratios on the same sample. Under these exemplary conditions, only the measurement valve is opened first. Once the vapor pressure has equilibrated, the pressure is recorded. After that, subsequent valves are opened. FIG. 10 illustrates that vapor pressure readings taken after equilibrium is reached following the opening of each valve. One (FIG. 10A) or several (FIG. 10B) additional measurement valves enable measurements to be made at multiple V/L ratios.

As noted above, in one embodiment, there is provided a method of analyzing a petroleum sample directly in a container, such that the sample is not exposed to an environment external to the container, comprising the steps of: (a) providing a container, the container comprising: a sample chamber capable of being fluidly connected to a sample source for flow-through sampling, and a measurement chamber, wherein the measurement chamber is capable of being fluidly connected to the sample chamber, the sample chamber comprising: an inlet valve and an outlet valve for flow-through sampling of the petroleum sample, a measurement valve for releasing the sample to the measurement chamber, and an inline filtering component disposed between the measurement valve and a point of connection of the sample chamber to the measurement chamber, the measurement chamber comprising: at least a first chamber fluidly connected to one or more sensors for measuring pressure and temperature, and a closure valve; (b) connecting the sample chamber to the sample source; (c) allowing the sample to flow from the sample source through the sample chamber via the inlet valve and the outlet valve, and thereafter closing the inlet valve and the outlet valve to obtain the sample to be analyzed in the sample chamber; (d) connecting the sample chamber to the measurement chamber; (e) moving the measurement valve to an open position to release the sample to the measurement chamber, wherein sample liquid is contained by the inline filtering component and wherein sample vapour enters and expands within the first chamber of the measurement chamber; and (f) measuring the pressure and temperature of the sample vapour in the measurement chamber.

In one embodiment, the sample chamber can be connected to the measurement chamber prior to step (c) of allowing the sample to flow from the sample source through the sample chamber and obtaining the sample to be analyzed in the sample chamber.

In another embodiment, the measurement chamber is fluidly connected to the sample chamber via a releasable connection.

FIG. 11 exhibits a schematic of an example of the above-noted embodiment, where the measurement and sample chamber can be separated and reconnected via a quick connection mechanism to provide increased usability. In this embodiment, there are two primary volumes which are constituted of various sub-volumes separated by the aforementioned valves. In this two-expansion measurement apparatus, volume 1 is constituted of V1,1+V1,2 and adjoined via the quick connection mechanism. Volume 2 is constituted of sub-volumes V1,1+V1,2+V'2. and separated from the last measurement sub volume via a valve.

In some embodiments the measurement chamber is completely evacuated and subject to a complete vacuum. This results in the sample immediately boiling upon opening volume 1 valve and increases the rate of which the system will equilibrate. An inline filtering component ("Expansion Union" shown in FIG. 11) is used in this embodiment to limit sample splatter upon opening valve 1 and over the duration of the expansion. This mitigates the need to thoroughly clean the measurement chamber post test and reduces the possibility of cross sample contamination of the measurement chamber in subsequent repeated use. Sample liquid is contained by the filtering component and is confined within the 'V1,1' sub volume in FIG. 11A whereas vapour expansion is uninhibited.

In some embodiments where there are multiple expansions, valves can be used to divide the measurement sub-volumes and actuated after the appropriate time has elapsed to ensure that the vapour expansion has reached a complete equilibrium. In some embodiments, the time duration of the expansion can be shortened and the final vapour expansion can be extrapolated to predict the final equilibrium pressure.

FIGS. 12A and B illustrates the specific components used in this embodiment of the measurement and sample chamber respectively, and used in the experiments that follow. Multiple valves are used to divide the separate measurement sub-volumes. Barbed outlets can be used to enable flexible tubing to the sample inlets and outlets for flow-through sampling. Optionally, these can be replaced with alternative connectors (e.g. quick connection mechanisms). In this embodiment, pressure and temperature measurement is integrated into a single USB communication sensor (ESI-Tec GS4200-USB, USB powered digital pressure transducer was used).

In some embodiments, where the sample chamber is reused—cleaning is required to avoid cross sample contamination. Specific components can be added to some embodiments to limit the sample contact with the measurement sensor to reduce efforts in measurement chamber cleaning and sensor foiling. In some embodiments, illustrated in FIGS. 12A and B, the measurement chamber can be vented by connection to a vacuum apparatus. Directional flow of sample vapour towards to the sensor can only be enabled with the use of an expansion union, which rapidly increases the internal diameter of the sample chamber (Swagelok: SS-810-6 Reducing/Expansion Union was used). This limits sample liquid from entering the measurement chamber by providing ample head space and cross-sectional area at the sample liquid/vapour interface during boiling. This promotes free flow of sample vapour but mitigates liquid splashing and possible foiling of the sensor. In some embodiments, the vacuum apparatus consists of both a vacuum trap and a vacuum pump. The vacuum trap is implemented to remove all vapour and liquid components and prevent vapour build-up in the vacuum pump thus maintaining vacuum efficiency and longevity.

In some embodiments, the sample port can be reused. The sample port requires cleaning prior to reuse to limit cross sample contamination. In this embodiment, the sample port is separated from the measurement chamber and costly sensing components. The vacuum apparatus was connected to sample port outlet. 50 mL of varsol (a mineral spirit used as a cleaning agent) was drawn through the sample port via vacuum using the same flow-through technique used in sampling. This process was repeated while toggling both inlet and outlet valves. 50 mL of varsol was drawn in the reverse direction (i.e. from 'outlet' to 'inlet'). To ensure that the cleaning protocol was adequate in limiting cross sample contamination, sequential and alternating tests were conducted with the prerequisite cleaning steps, FIG. 20. Firstly, alkanes with known vapour pressures were measured. Secondly, the sample port was cleaned using the described cleaning protocol and the measurement chamber was vented using the vacuum apparatus. Thirdly, a crude oil sample with unknown vapour pressure was measured. Lastly, the entire measurement apparatus was cleaned and a measurement with a known alkane was repeated to observe any deviation as result of cross contamination. The procedure was repeated with combinations of other known alkanes and unknown crude oil samples. Alternatively, combinations of crude oil blends can be measured in an alternating pattern to observe the intra-sample consistency and viability of the cleaning protocol in this embodiment, FIG. 21.

Vapor pressure measurements are typically calibrated using samples with known vapour pressures (i.e. pure alkanes). FIG. 14 illustrates the measured vapour expansion pressure of pentane over time to evaluate the rate of equilibration in comparison to known vapour pressure values of pentane. FIG. 16A illustrates measurement data obtained via the measurement apparatus of a select set of alkanes with known vapour pressures. In some embodiments, pentane is frequently used for calibration and evaluation due to its large vapour pressure. FIGS. 17A and B illustrates repeated vapour pressure measurements of pentane and its distribution, highlighting intra-sample variability and the experimental repeatability of the device.

Vapor pressure measurements have a strong dependence on temperature. Therefore the temperature of the chamber must be controlled and/or measured. In some embodiments of the method described herein, the temperature may be controlled by immersing the entire portable apparatus (sample chamber and vapor chamber) in a temperature-controlled environment, such as a water bath, oven, silicone bath, temperature-controlled plate, etc. Optionally, elements that heat the chambers (e.g. Pelletier heating elements) and measure the temperature (e.g. thermocouple, thermometer) may be permanently affixed to the exterior of the apparatus and actively maintain the temperature at one or more fixed set points during the measurement. Sample data of controlled temperature measurements are illustrated in FIGS. 15A, B and FIG. 16B. A temperature-vapour pressure curve for acetone, hexane and octane are constructed using measured vapour pressure values under temperature controlled environments and compared to known temperature curves where available. This was used to confirm the devices' ability to measure the temperature dependency of vapour pressure for various known alkanes.

In other embodiments, the temperature of the chamber is accurately monitored throughout the duration of the expansion. This can be done with separate temperature and pressure sensors or in some embodiments, an integrated sensing solution can be used (FIG. 12A). The use of real-time temperature correction can be used to eliminate the need for temperature control. In this embodiment, temperature correction curves (FIG. 18) can used to predict the vapour pressure at a desired temperature from the measured vapour pressure at a given experimental and monitored temperature. Light crude oils (>37° API and <42° API) and heavy crude oils (<20° API) samples are subject to separate temperature correction curves. Given a measured vapour pressure at some experimental temperature—a temperature correction curve is selected and used to project the vapour pressure at the desired temperature. Linear interpolation is used in many instances where a measured vapour pressure will reside in between two correction curves. Pressures outside the maximum and minimum correction curves require extrapolation. FIGS. 19A and B illustrates an example of temperature correction for various temperature controlled tests at −12, 7, 21 and 35° C. Often samples require vapour pressure measurements at 37.8° C. to conform to industry test standards (ASTM D6377). FIG. 23 illustrates various crude oil blends and condensates measured at various experimental temperatures and temperature corrected to yield comparable vapour pressure measurements to reference instrument results.

As noted above, the step of measuring the pressure and temperature of the sample vapour in the measurement chamber can occur after the sample vapour expansion has reached equilibrium; optionally, the method can further comprise a step of reporting the equilibrium vapor pressure of the sample to a user. In an alternate embodiment, the method further comprises a step of reporting the equilibrium vapor pressure of the sample to a user, either at the temperature in the vapor chamber or at another reference temperature, wherein the step of reporting occurs prior to the sample vapour expansion reaching equilibrium, and an extrapolation algorithm is used to predict the equilibration vapour pressure based on elapsed expansion time and the time variation of the pressure and temperature measurements. The extrapolation algorithm to predict equilibrium vapor pressure from the time-varying pressure and temperature measurements incorporates statistical correlations to a library of previous measurements in the container that were allowed to reach equilibrium.

Thus, in some embodiments, the measurement time can be shortened to less than the time required for the vapour expansion to equilibrate. Continuous pressure readings of the measurement chamber over multiple volume expansions can be recorded, as illustrated in FIG. 22, and used as part of an extrapolation algorithm to predict the equilibration vapour pressure given the elapsed expansion time and current measurement pressure. As will be appreciated by the skilled worker, the live reporting of predicted vapour pressure based on time evolution of pressure in the chamber (noting there can be multiple expansions in some embodiments) is important because it allows very rapid measurements to be made (e.g. before a truck has a chance to fully offload).

In some embodiments, the mechanism for communication of the sensor can vary between wireless or wired connectivity. FIG. 24 illustrates the intra-sensor and intra-sample variability between (1) two oil blends and (2) bluetooth and USB sensors used in some embodiments (Transducer Direct CirrusSense TDWLB wireless Bluetooth pressure sensor and ESI-Tec GS4200 USB powered digital pressure transducer were used).

In one embodiment, the closure valve of the measurement chamber is fluidly connected to a vacuum apparatus, and the measurement chamber is evacuated and subject to a vacuum prior to each sample measurement. In another embodiment, the measurement chamber is pressurized with an inert gas following evacuation, prior to each sample measurement. In yet another embodiment, the measurement chamber is maintained at atmospheric pressure prior to each sample measurement, and an algorithm is used to predict a free expansion vapour pressure of the sample vapour based on a measured partial expansion pressure of the sample vapour.

Thus, in some embodiments, the measurement chamber is maintained at atmospheric pressures instead of either being completely evacuated, or filled with an inert gas. This mitigates the need for a vacuum apparatus at the experimental site. The sample chamber remains at a vacuum in the sub-volume, V1,1, (FIG. 11A). A partial vacuum is established in volume 1, constituted by V1,1+V1,2, upon connection of the sample and measurement chambers. The starting measurement chamber pressure is uncontrolled here and can vary between 0 and 1 atm., but can be accounted for algorithmically. FIG. 25 illustrates the correlation between a corrected 'partial pressure' vapour pressure expansion and the typical vapour pressure expansion described in other embodiments. The strong linear correlation between these two parameters can be leveraged to predict true vapour pressures and vapour pressure at other temperatures.

In one embodiment, the container can be fluidly connected to one or more additional containers configured to measure one or more additional properties of the sample (such as sample weight, density or specific gravity, sulphur content, water content, viscosity, colour, and/or refractive index).

In some embodiments, the reader comprises at least one source of radiation and a detector, and the sample container has at least one face that is transparent to the radiation. FIG. 26 illustrates embodiments of the reader and sample container. In some embodiments, the reader contains at least one source of radiation and a detector and the sample container has at least one face that is transparent to the radiation.

As shown in the embodiment in FIG. 26A, the source and detector are configured such that the detector detects scattered or reflected radiation. In some embodiments, the detector detects transmitted radiation (FIG. 26B). Radiation frequencies are chosen to select for specific characteristics of the liquid. In some embodiments, the radiation is electromagnetic in X-ray frequencies, with wavelength spanning all or part of the range between 0.1 and 10 nm. In these embodiments, the detector records transmittance, absorbance and/or fluorescence from the X-rays incident on the sample and these values, as a function of x-ray frequency, are used to calculate the content of one or more heavy elements (e.g. sulphur, chlorine, nickel, vanadium, lead). In some embodiments, the radiation is electromagnetic radiation in the infrared frequency (IR) range, with wavelength spanning all or part of the range from 700 nm to 10 μm. In some embodiments, IR absorbance, transmittance, scattering and/or fluorescence is used to calculate the content of dissolved and/or suspended water in the petroleum liquid. In some embodiments, the IR absorbance, transmittance, scattering and/or fluorescence is used to calculate the content of the light fractions (methane, ethane, propane, butane, isobutene, CO2, H2S etc.). In some embodiments, the radiation is electromagnetic radiation in the microwave frequency range, with wavelength spanning all or part of the range from 1 mm to 1 m. In some embodiments, microwave absorbance, transmittance, scattering and/or fluorescence is used to calculate the content of dissolved and/or suspended water in the petroleum liquid. In some embodiments, the radiation is electromagnetic radiation in the ultraviolet frequency (UV) range, with wavelength spanning all or part of the range from 100 nm to 400 nm. In some embodiments, UV absorbance, transmittance, scattering and/or fluorescence is used to calculate the content of dissolved and/or suspended water in the petroleum liquid. In some embodiments, the radiation is electromagnetic radiation in the visible frequency range, with wavelength spanning all or part of the range from 400 nm to 800 nm. In some embodiments, visible absorbance, transmittance, scattering and/or fluorescence is used to calculate the content of dissolved and/or suspended water in the petroleum liquid. In some embodiments, visible absorbance, transmittance, scattering and/or fluorescence is used to calculate the color of the petroleum liquid. In some embodiments, visible absorbance, reflectance transmittance, and/or scattering is used to calculate the refractive index of the petroleum liquid.

In some embodiments, the reader may contain multiple sources and detectors of radiation at different frequencies. In some embodiments, a combination of absorbance, transmittance, scattering and/or fluorescence at several electromagnetic frequency ranges (e.g. UV, visible, IR, microwave) may be used to calculate the content of dissolved and/or suspended water in the petroleum liquid.

In some embodiments, the radiation is acoustic and/or ultrasound radiation and acoustic absorbance, transmittance, reflectance, and/or scattering from the sample container is used to calculate the density and/or the viscosity of the liquid.

The system as described herein may include a processing unit connected to the pressure transducer. The pressure transducer may connect to the processing unit wirelessly, via a WiFi, bluetooth or RF connection. The processing unit may also function as the CPU for all measurements done by the reader or reader array. The processing unit may also transmit data to an external CPU that co-ordinates all measurements. This external CPU may also be an internet-connected server that communicates with the pressure transducer via an internet connection.

FIG. 3 provides an exemplary schematic of different reader configurations for a sample chamber array. FIG. 3A shows one embodiment where all chambers may connect to the same reader at different locations. FIG. 3B shows one embodiment where the chambers may be detached from one another and connected to an array of readers. In some embodiments, each reader communicates with a central processing unit via a physical connection, wireless connection (Bluetooth, WiFi, satellite), and/or via the internet.

All publications, patents and patent applications mentioned in this Specification are indicative of the level of skill of those skilled in the art to which this invention pertains and are herein incorporated by reference to the same extent as if each individual publication, patent, or patent applications was specifically and individually indicated to be incorporated by reference.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

The embodiments of the invention in which an exclusive property or privilege is claimed are defined as follows:

1. A method of analyzing a sample directly in a container, comprising the steps of:
    providing a container;
    obtaining a sample to be analyzed in the container, the sample being obtained from a sample source;
    performing one or more measurements on the sample directly in the container with a reader; and
    visually outputting the one or more measurements to a device;
    wherein two or more of the containers are positioned in an array, wherein each of the two or more containers are fluidly connected with each other.

2. The method of claim 1, wherein the sample is a petroleum or petroleum liquid sample.

3. The method of claim 1, wherein the sample is measured directly in the container without removal of sample from the container, such that the sample is not exposed to an external environment to the container.

4. The method of claim 1, wherein the one or more measurements comprise weighing the sample, density or specific gravity, vapour pressure, sulphur content, water content, viscosity, colour, and/or refractive index.

5. The method of claim 4, wherein the density of the sample is determined independent of the temperature at the time of measurement; or, wherein the density depends on the temperature at the time of sampling.

6. The method of claim 1, wherein the sampling source is a pipeline, storage tank, tanker truck, or rail car.

7. The method of claim 1, wherein the sample is provided in each of the two or more containers, such that the sample is capable of being analyzed in each of the two or more containers; wherein the method further comprises the step of:
    performing a replicate analysis of the sample in each of the two or more containers; or
    performing a unique analysis of the sample in each of the two or more containers.

8. The method of claim 1, wherein the one or more measurements comprise determining the vapour pressure of the sample.

9. The method of claim 8, wherein the sample is obtained from the sample source at the pressure of the source, wherein the pressure of the sample is maintained during transport and/or testing of the sample.

10. The method of claim 1, wherein the container is in communication with one or more other containers via a central processing unit (CPU).

11. The method of claim 1, wherein:
    (i) one or more of the containers and/or one or more of the readers comprise a processor for processing the one or more measurements to obtained processed data or
    (ii) the measurements obtained from the sample are analyzed by external processors to obtain processed data.

12. The method of claim 3, wherein the sample is a petroleum sample.

13. A system for analyzing a sample directly in a container, the system comprising:
    one or more sample containers for storing a sample to be analyzed, the sample being obtained from a sample source; and
    one or more sample readers for directly analyzing the sample in the one or more sample containers to provide one or more measurements of the sample;
    wherein the one or more sample containers are in communication with one or more other containers via a central processing unit (CPU).

14. The system of claim 13, further comprising a reader for visualizing the one or more measurements.

15. The system of claim 13, comprising two or more sample containers.

16. The system of claim 15, further comprising one or more of the following characteristics:
    (i) the two or more sample containers are fluidly connected to each other;
    (ii) the two or more sample containers are fluidly connected to each other and the sample is capable of being analyzed in each of the two or more containers;
    (iii) the one or more measurements comprise weight of the sample, density or specific gravity, vapour pressure, sulphur content, water content, viscosity and/or refractive index; and
    (iv) the system further comprises a processor.

17. The system of claim 15, wherein the two or more sample containers are positioned in an array, wherein each of the two or more sample containers are fluidly connected with each other.

18. The system of claim 13, wherein the CPU comprises one or more of the following characteristics:
    (i) the CPU is a cloud server which connects the one or more containers through the internet;
    (ii) the CPU communicates through a local connection; and
    (iii) the CPU is integral with one or more of the containers, one or more readers, or both.

19. The system of claim 13, wherein:
    (i) one or more of the containers and/or one or more of the readers comprise a processor for processing the one or more measurements to obtained processed data; or
    (ii) the measurements obtained from the sample are analyzed by external processors to obtain processed data.

20. A method of analyzing a petroleum sample directly in a container, such that the sample is not exposed to an environment external to the container, comprising the steps of:
(a) providing a container, the container comprising:
a sample chamber capable of being fluidly connected to a sample source for flow-through sampling, and
a measurement chamber, wherein the measurement chamber is capable of being fluidly connected to the sample chamber,
the sample chamber comprising:
an inlet valve and an outlet valve for flow-through sampling of the petroleum sample,
a measurement valve for releasing the sample to the measurement chamber, and
an inline filtering component disposed between the measurement valve and
a point of connection of the sample chamber to the measurement chamber,
the measurement chamber comprising:
at least a first chamber fluidly connected to one or more sensors for measuring pressure and temperature, and
a closure valve;
(b) connecting the sample chamber to the sample source;
(c) allowing the sample to flow from the sample source through the sample chamber via the inlet valve and the outlet valve, and thereafter closing the inlet valve and the outlet valve to obtain the sample to be analyzed in the sample chamber;
(d) connecting the sample chamber to the measurement chamber;
(e) moving the measurement valve to an open position to release the sample to the measurement chamber, wherein sample liquid is contained by the inline filtering component and wherein sample vapour enters and expands within the first chamber of the measurement chamber; and
(f) measuring the pressure and temperature of the sample vapour in the measurement chamber;
wherein the container can be fluidly connected to one or more additional containers configured to measure one or more additional properties of the sample, the method further comprising:
connecting the container to one or more additional containers configures to measure one or more additional properties of the sample, and
measuring one or more additional properties of the sample.

21. The method of claim 20, further comprising one or more of the following characteristics:
(i) the measurement chamber is fluidly connected to the sample chamber via a releasable connection; and
(ii) (a) the step of measuring the pressure and temperature of the sample vapour in the measurement chamber occurs after the sample vapour expansion has reached equilibrium; or
(b) the method further comprises a step of reporting the equilibrium vapor pressure of the sample to a user, either at the temperature in the vapor chamber or at another reference temperature, wherein the step of reporting occurs prior to the sample vapour expansion reaching equilibrium, and an extrapolation algorithm is used to predict the equilibration vapour pressure based on elapsed expansion time and the time variation of the pressure and temperature measurements.

22. The method of claim 20, the method further comprising a step of reporting the equilibrium vapor pressure of the sample to a user, either at the temperature in the vapor chamber or at another reference temperature, wherein the step of reporting occurs prior to the sample vapour expansion reaching equilibrium, and an extrapolation algorithm is used to predict the equilibration vapour pressure based on elapsed expansion time and the time variation of the pressure and temperature measurements, and wherein the extrapolation algorithm to predict equilibrium vapor pressure from the time-varying pressure and temperature measurements incorporates statistical correlations to a library of previous measurements in the container that were allowed to reach equilibrium.

23. The method of claim 20, wherein:
(i) the closure valve of the measurement chamber is fluidly connected to a vacuum apparatus, and the measurement chamber is evacuated and subject to a vacuum prior to each sample measurement; or
(ii) the measurement chamber is maintained at atmospheric pressure prior to each sample measurement, and an algorithm is used to predict a free expansion vapour pressure of the sample vapour based on a measured partial expansion pressure of the sample vapour.

24. The method of claim 20, wherein the one or more additional properties of the sample are selected from sample weight, density or specific gravity, sulphur content, water content, viscosity, colour, or refractive index.

* * * * *